US011857371B2

(12) United States Patent
Lee et al.

(10) Patent No.: US 11,857,371 B2
(45) Date of Patent: *Jan. 2, 2024

(54) ULTRASOUND METHOD AND APPARATUS FOR PROCESSING ULTRASOUND IMAGE TO OBTAIN MEASUREMENT INFORMATION OF AN OBJECT IN THE ULTRASOUND IMAGE

(71) Applicant: SAMSUNG MEDISON CO., LTD., Gangwon-do (KR)

(72) Inventors: Seung-ju Lee, Gangwon-do (KR); Yoon-woo Jun, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 275 days.

This patent is subject to a terminal disclaimer.

(21) Appl. No.: 17/314,501

(22) Filed: May 7, 2021

(65) Prior Publication Data

US 2021/0267575 A1  Sep. 2, 2021

Related U.S. Application Data

(63) Continuation of application No. 14/739,734, filed on Jun. 15, 2015, now Pat. No. 11,000,261.

(30) Foreign Application Priority Data

Dec. 5, 2014  (KR) .................. 10-2014-0174277

(51) Int. Cl.
*A61B 8/00* (2006.01)
*A61B 8/08* (2006.01)
(Continued)

(52) U.S. Cl.
CPC .............. *A61B 8/467* (2013.01); *A61B 8/461* (2013.01); *A61B 8/469* (2013.01); *A61B 8/5207* (2013.01);
(Continued)

(58) Field of Classification Search
None
See application file for complete search history.

(56) References Cited

U.S. PATENT DOCUMENTS 6,692,436 B1  2/2004  Bluth et al.
9,492,240 B2  11/2016  Itkowitz et al.
(Continued)

FOREIGN PATENT DOCUMENTS

CN   103513920 A    1/2014
EP     2742868 A1   6/2014
(Continued)

OTHER PUBLICATIONS

Korean Office Action dated May 20, 2021 issued in Korean Patent Application No. 10-2014-0174277 (with English translation).
(Continued)

*Primary Examiner* — Joel Lamprecht
*Assistant Examiner* — Nyrobi Celestine
(74) *Attorney, Agent, or Firm* — Morgan, Lewis & Bockius LLP

(57) ABSTRACT

An ultrasound apparatus includes: a display unit configured to display on an ultrasound image a measuring device image including a plurality of measuring points which indicate points on the ultrasound image that are to be measured, and an adjusting portion for adjusting the plurality of measuring points; an input unit configured to receive a touch input for changing a position of the adjusting portion; and a controller configured to adjust a position of at least one of the plurality of measuring points based on the changed position of the adjusting portion, and to obtain a measurement value based on positions of the plurality of measuring points including the at least one measuring point, the position of which is adjusted, wherein the plurality of measuring points are disposed apart from the adjusting portion.

22 Claims, 27 Drawing Sheets

(51) Int. Cl.
  *G06F 3/0488* (2022.01)
  *G06F 3/0484* (2022.01)
  *G06F 3/04845* (2022.01)
  *G06F 3/04886* (2022.01)
  *G06T 7/00* (2017.01)

(52) U.S. Cl.
  CPC .......... *A61B 8/5215* (2013.01); *A61B 8/5223* (2013.01); *G06F 3/0484* (2013.01); *G06F 3/0488* (2013.01); *G06F 3/04845* (2013.01); *G06F 3/04886* (2013.01); *A61B 8/4405* (2013.01); *A61B 8/46* (2013.01); *A61B 8/465* (2013.01); *A61B 8/5292* (2013.01); *G06F 2203/04804* (2013.01); *G06T 7/0012* (2013.01)

(56) References Cited

U.S. PATENT DOCUMENTS

| | | |
|---|---|---|
| 10,426,438 B2 | 10/2019 | Roh et al. |
| 10,687,780 B2 | 6/2020 | Fukai et al. |
| 2002/0052941 A1 | 5/2002 | Patterson |
| 2008/0221446 A1 | 9/2008 | Washburn |
| 2009/0306514 A1 | 12/2009 | Imamura et al. |
| 2010/0004539 A1 | 1/2010 | Chen |
| 2011/0169748 A1 | 7/2011 | Tse et al. |
| 2011/0282199 A1 | 11/2011 | Lee |
| 2011/0282205 A1 | 11/2011 | Kim |
| 2011/0313291 A1 | 12/2011 | Chono |
| 2013/0072797 A1 | 3/2013 | Lee |
| 2013/0169674 A1 | 7/2013 | Kim |
| 2013/0169782 A1 | 7/2013 | Choi |
| 2013/0201210 A1 | 8/2013 | Vaddadi |
| 2013/0202169 A1 | 8/2013 | Lee |
| 2013/0261449 A1 | 10/2013 | Tashiro |
| 2013/0321286 A1 | 12/2013 | Petruzelli |
| 2013/0324850 A1 | 12/2013 | Petruzzelli et al. |
| 2013/0345563 A1 | 12/2013 | Stuebe |
| 2013/0345566 A1 | 12/2013 | Weitzel |
| 2014/0029815 A1 | 1/2014 | Kadir |
| 2014/0059486 A1* | 2/2014 | Sasaki .................. A61B 8/0866 715/810 |
| 2014/0071069 A1 | 3/2014 | Anderson |
| 2014/0082542 A1 | 3/2014 | Zhang et al. |
| 2014/0114190 A1 | 4/2014 | Chiang |
| 2014/0121524 A1 | 5/2014 | Chiang et al. |
| 2014/0148719 A1 | 5/2014 | Yang |
| 2014/0152654 A1 | 6/2014 | Yoo et al. |
| 2014/0181717 A1 | 6/2014 | Lahti |
| 2014/0221835 A1 | 8/2014 | Ota |
| 2014/0378837 A1 | 12/2014 | Fujiwara |
| 2015/0011886 A1 | 1/2015 | Radulescu |
| 2015/0297179 A1* | 10/2015 | Mander ................ A61B 8/4427 600/440 |
| 2015/0331576 A1 | 11/2015 | Piya |
| 2016/0007965 A1 | 1/2016 | Murphy |
| 2016/0179326 A1 | 6/2016 | Aswathanarayana et al. |

FOREIGN PATENT DOCUMENTS

| | | |
|---|---|---|
| EP | 2767955 A1 | 8/2014 |
| EP | 2777506 A1 | 9/2014 |
| EP | 2921115 A1 | 9/2015 |
| JP | H03-261813 A | 11/1991 |
| JP | H04-53546 A | 2/1992 |
| JP | H06-125893 A | 5/1994 |
| JP | H06-178773 A | 6/1994 |
| JP | H11-113901 A | 4/1999 |
| JP | 2012-019824 A | 2/2012 |
| JP | 2014-094246 A | 5/2014 |
| KR | 10-2010-0110893 A | 10/2010 |
| KR | 10-2012-0040687 A | 4/2012 |
| KR | 10-2014-0071650 A | 6/2014 |
| KR | 10-2015-0108693 A | 9/2015 |
| WO | 2009/090686 A1 | 7/2009 |

OTHER PUBLICATIONS

U.S. Office Action dated Dec. 7, 2022 issued in U.S. Appl. No. 17/314,577.
U.S. Notice of Allowance dated Jan. 12, 2021 issued in U.S. Appl. No. 14/739,734.
European Office Action dated Jul. 9, 2020 issued in European Patent Application No. 15165356.5.
The Extended European Search Report dated Apr. 25, 2016 issued in European Patent Application No. 15165356.5.
The Second Office Action dated Aug. 10, 2020 issued in Chinese Patent Application No. 201510882396.1 (with English translation).
The First Office Action dated Oct. 25, 2019 issued in Chinese Patent Application No. 201510882396.1 (with English translation).

* cited by examiner

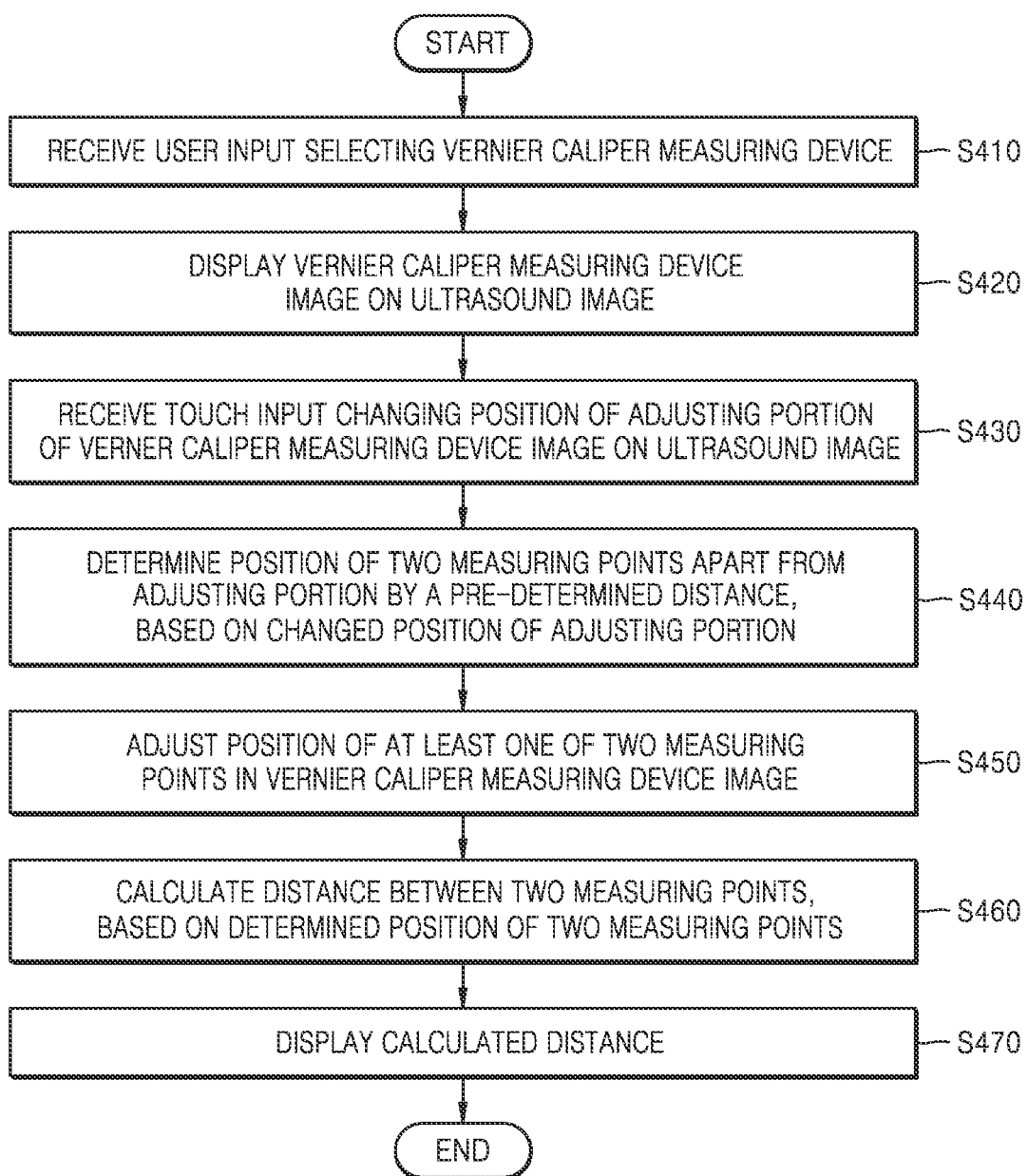

ULTRASOUND METHOD AND APPARATUS FOR PROCESSING ULTRASOUND IMAGE TO OBTAIN MEASUREMENT INFORMATION OF AN OBJECT IN THE ULTRASOUND IMAGE

RELATED APPLICATION

This application is a continuation of U.S. patent application Ser. No. 14/739,734, filed on Jun. 15, 2015, which claims the benefit of Korean Patent Application No. 10-2014-0174277, filed on Dec. 5, 2014, in the Korean Intellectual Property Office, the disclosure of which is incorporated herein in its entirety by reference.

BACKGROUND

1. Field

One or more exemplary embodiments relate to an ultrasound image processing method that obtains measurement information with respect to an object in an ultrasound image, based on an input of a user, and an ultrasound apparatus for executing the method.

2. Description of the Related Art

Ultrasound diagnosis apparatuses transmit ultrasound signals generated by transducers of a probe to an object and receive echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

Meanwhile, sometimes a user has to measure a size, angle, area, or volume of an internal organ of a patient from an ultrasound image. Also, there is an occasion when a user needs to extract a characteristic of a graph or a figure indicated in an ultrasound image. In addition, a user may passively obtain a measurement value with respect to a measurement item that is to be measured, by using a measuring device, such as a caliper displayed in an ultrasound image.

In order to increase the accuracy of a diagnosis, there is a need to provide a method and apparatus for increasing an accuracy of a measurement value by precisely and easily configuring a measurement item that a user aims to measure. In detail, a user interface for precisely configuring a measuring point in an ultrasound image by a simple input and for rapidly obtaining measurement information is required for a user to obtain measurement value.

SUMMARY

One or more exemplary embodiments include an ultrasound image processing method that measures an object indicated in an ultrasound image by using a measuring device which is determined according to an input of a user, and an ultrasound apparatus for executing the method.

Additional aspects will be set forth in part in the description which follows and, in part, will be apparent from the description, or may be learned by practice of the presented embodiments.

According to one or more exemplary embodiments, an ultrasound apparatus includes a display unit configured to display on an ultrasound image a measuring device image including a plurality of measuring points which indicate points on the ultrasound image that are to be measured, and an adjusting portion for adjusting the plurality of measuring points; a user input unit configured to receive a touch input for changing a position of the adjusting portion; and a controller configured to adjust a position of at least one of the plurality of measuring points based on the changed position of the adjusting portion, and to obtain a measurement value based on positions of the plurality of measuring points including the at least one measuring point, the position of which is adjusted, wherein the plurality of measuring points are disposed apart from the adjusting portion.

The controller may adjust the position of the at least one of the plurality of measuring points by changing at least one of a position and a shape of the measuring device image, when the touch input for changing the position of the adjusting portion is received.

The controller may adjust the position of the at least one of the plurality of measuring points by adjusting a size of the measuring device image, when the touch input for changing the position of the adjusting portion is received.

The controller may adjust the position of the at least one of the plurality of measuring points by rotating the measuring device image, when the touch input for changing the position of the adjusting portion is received.

The measuring device image may have a shape that two partial images cross each other based on a reference point. The controller may adjust the position of the at least one of the plurality of measuring points by rotating the two partial images based on the reference point, when the touch input for changing the position of the adjusting portion is received.

The display unit may display the obtained measurement value on the measuring device image.

The display unit may display the measuring device image in a half-transparent way so that an area of the ultrasound image, which overlaps the measuring device image, is not covered by the measuring device image.

The touch input for changing the position of the adjusting portion may include a user input of touching and dragging the adjusting portion.

The user input unit may receive a touch input of ending the user input of touching and dragging the adjusting portion. The display unit may display on the ultrasound image a button image for storing the obtained measurement value in correspondence with the ultrasound image, when the user input of touching and dragging the adjusting portion is ended.

The input unit may receive a touch input of ending the user input of touching and dragging the adjusting portion. The display unit may delete the measuring device image and display on the ultrasound image a button image for re-adjusting the positions of the plurality of measuring points, when the user input of touching and dragging the adjusting portion is ended.

According to one or more exemplary embodiments, a method of processing an ultrasound image includes: displaying on the ultrasound image a measuring device image including a plurality of measuring points which indicate points on the ultrasound image that are to be measured, and an adjusting portion for adjusting the plurality of measuring points; receiving a touch input for changing a position of the adjusting portion; and adjusting a position of at least one of the plurality of measuring points, based on the changed position of the adjusting portion, and obtaining a measurement value, based on positions of the plurality of measuring points including the at least one measuring point, the position of which is adjusted, wherein the plurality of measuring points are disposed apart from the adjusting portion.

The adjusting of the position of the at least one of the plurality of measuring points may include adjusting the position of the at least one of the plurality of measuring points, by changing at least one of a position and a shape of the measuring device image, when the touch input for changing the position of the adjusting portion is received.

The adjusting of the position of the at least one of the plurality of measuring points may include adjusting the position of the at least one of the plurality of measuring points by adjusting a size of the measuring device image, when the touch input for changing the position of the adjusting portion is received.

The adjusting of the position of the at least one of the plurality of measuring points may include adjusting the position of the at least one of the plurality of measuring points by rotating the measuring device image, when the touch input for changing the position of the adjusting portion is received.

The measuring device image may have a shape that two partial images cross each other based on a reference point. The adjusting of the position of the at least one of the plurality of measuring points may include adjusting the position of the at least one of the plurality of measuring points by rotating the two partial images based on the reference point, when the touch input for changing the position of the adjusting portion is received.

The method may further include displaying the obtained measurement value on the measuring device image.

The displaying of the measuring device image on the ultrasound image may include displaying the measuring device image in a half-transparent way so that an area of the ultrasound image, which overlaps the measuring device image, is not covered by the measuring device image.

The touch input for changing the position of the adjusting portion may include a user input of touching and dragging the adjusting portion.

The method may further include receiving a touch input of ending the user input of touching and dragging the adjusting portion, and displaying on the ultrasound image a button image for storing the measurement value in correspondence with the ultrasound image, when the user input of touching and dragging the adjusting portion is ended.

The method may further include receiving a touch input of ending the user input of touching and dragging the adjusting portion, and deleting the measuring device image and displaying on the ultrasound image a button image for re-adjusting the positions of the plurality of measuring points, when the user input of touching and dragging the adjusting portion is ended.

BRIEF DESCRIPTION OF THE DRAWINGS

Embodiments of the invention now will be described more fully hereinafter with reference to the accompanying drawings, in which reference numerals denote structural elements.

FIG. 4 is a flowchart of a method of providing a measuring device via an ultrasound apparatus, according to an embodiment;

DETAILED DESCRIPTION

Figure 1:
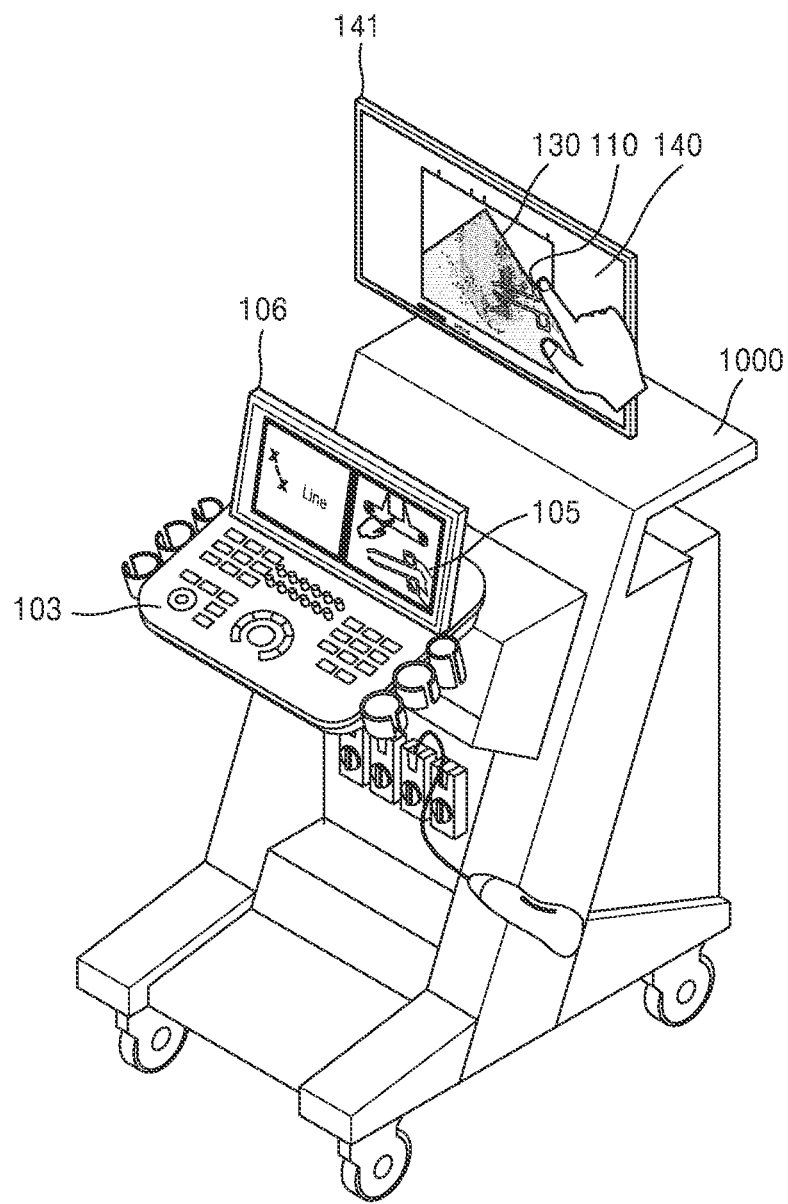
FIG. 1 is a view of an ultrasound apparatus according to an embodiment.

Hereinafter, the terms used in the specification will be briefly defined, and the embodiments will be described in detail.

The terms used in this specification are those general terms currently widely used in the art in consideration of functions regarding the present invention, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. The object may refer to a part of a human body. For example, the object may include organs, such as the liver, the heart, the brain, a breast, and the abdomen, or a fetus.

In the present specification, the term "user" may refer to a medical professional, such as a doctor, a nurse, a medical laboratory technologist, a medical imaging technologist, or a sonographer, but the user is not limited thereto.

Throughout the specification, the term "measuring device" may refer to a measuring application that receives a user input for configuring a position of a measuring point and provides measurement information with respect to an object in a ultrasound image based on the configured position of the measuring point, by using an image indicating a measuring point in an ultrasound image as a medium.

The term "measuring device image" refers to a measuring point, and may refer to an image medium of a graphic user interface for receiving the user input configuring the position of the measuring point.

For example, when the ultrasound apparatus receives a user input selecting a measuring device for measuring a distance, the ultrasound apparatus may display on the ultrasound image the measuring device image indicating two measuring points in the ultrasound image. Also, the ultrasound apparatus may receive a user input configuring the position of the measuring point via the measuring device image. When receiving the user input configuring the position of the measuring point, the ultrasound apparatus may measure a distance based on the configured position of the measuring point.

Reference will now be made in detail to embodiments, examples of which are illustrated in the accompanying drawings. In this regard, the present embodiments may have different forms and should not be construed as being limited to the descriptions set forth herein. Also, parts in the drawings unrelated to the detailed description are omitted to ensure clarity of the inventive concept. Like reference numerals refer to like elements throughout.

FIG. 1 is a diagram illustrating an ultrasound apparatus 1000 according to exemplary embodiments. The ultrasound apparatus 1000 may include a display unit 141, an input unit 103, and a controller (not shown). The input unit 103 may further include a predetermined screen, or a display panel or a touch screen 106 for visually providing information to a user, in addition to an input device for a user to input data, commands or requests to the ultrasound apparatus 1000. Also, the display unit 141 may operate as a touch screen receiving a user's touch input.

Referring to FIG. 1, the display unit 141 of the ultrasound apparatus 1000 may display an ultrasound image 130 on the touch screen 106. Also, the ultrasound apparatus 1000 may display on the ultrasound image 130 a measuring device image 110 for measuring an object included in the ultrasound image 130.

The ultrasound apparatus 1000 may determine one from among a plurality of measuring devices, based on a user input that is input through the input unit 103. For example, the ultrasound apparatus 1000 may determine one from among the plurality of measuring devices, when receiving the user input selecting the measuring device.

When the ultrasound apparatus 1000 determines one from among the plurality of measuring devices, the ultrasound apparatus 1000 may display a measuring device image 110 corresponding to the measuring device, on the ultrasound image 130. For example, when the ultrasound apparatus 1000 receives a user input selecting an icon 105 indicating a length measuring device for measuring a length of a specific part of an organ or a specific bone, the ultrasound apparatus 1000 may display a length measuring device image 110 corresponding to the length measuring device, on the ultrasound image 130.

The measuring device image 110 may include a measuring point which indicates a point on the ultrasound image that is to be measured. Also, the measuring device image 110 may include an adjusting portion for receiving a user input adjusting a position of the measuring point. In this case, the measuring point may be disposed apart from the adjusting portion. Accordingly, the user may precisely configure the measuring portion, without covering with a finger the measuring portion on the ultrasound image.

Also, the ultrasound apparatus 1000 may receive a touch input changing a position of the adjusting portion.

Also, the ultrasound apparatus 1000 may adjust a position of at least one of the plurality of measuring points, based on the changed position of the adjusting portion, and may obtain a measurement value, based on a position of the plurality of measuring points including the at least one measuring point, the position of which is adjusted.

Also, the ultrasound apparatus 1000 may display the obtained measurement value.

When the ultrasound apparatus 1000 receives a touch input with respect to the adjusting portion, the ultrasound apparatus 1000 may change a position of the adjusting portion and the measuring point, in the ultrasound image, by changing at least one of a position and a shape of the measuring device image 110.

For example, when receiving the touch input with respect to the adjusting portion, the ultrasound apparatus 1000 may determine the position of the measuring point based on the position of the adjusting portion. Also, when the position of the measuring point is determined, the ultrasound apparatus 1000 may display the measuring point by shifting the measuring point in the measuring device image. In this case, the ultrasound apparatus 1000 may shift the measuring point by changing at least one of the shape and the position of the measuring device image 110.

Also, when the position of the measuring point is determined, the ultrasound apparatus 1000 may calculate a measurement value with respect to a measurement item corresponding to a measuring device that is selected based on the determined position of the measuring point. The measurement item may include information associated with a length, an angle, an area, and a volume.

Shapes of a measuring device image for measuring a distance may be a physical vernier caliper or a physical pincette. Also, shapes of a measuring device image for measuring an area may be the physical scissors. Also, shapes of a measuring device image for measuring an outline may be a physical pen. Accordingly, the user may instinctively recognize an interface method with respect to the measuring device.

Figure 2:
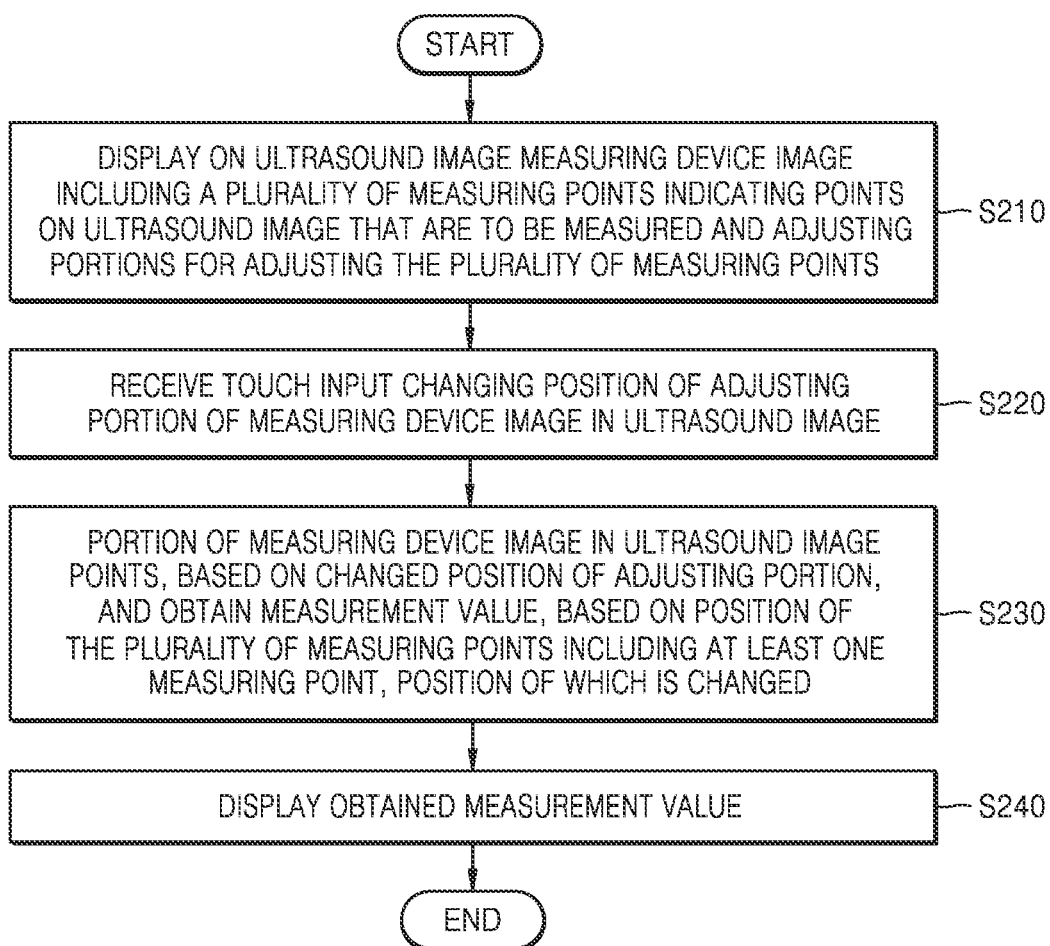
FIG. 2 is a flowchart of a method of obtaining a measurement value via an ultrasound apparatus, according to an embodiment.

FIG. 2 is a flowchart of a method of obtaining a measurement value via the ultrasound apparatus 1000, according to an embodiment.

The ultrasound apparatus 1000 may display a measuring device image including a plurality of measuring points, which indicate points on an ultrasound image that are to be measured, and an adjusting portion for adjusting the plurality of measuring points, on the ultrasound image, in operation S210.

The ultrasound apparatus 1000 may receive a user input selecting one from among a plurality of measuring devices.

The measuring devices may refer to a measuring application which receives a user input configuring a position of the measuring point, and provides a measurement value with respect to an object in an ultrasound image based on the position of the measuring point, by using an image indicating a point on an ultrasound image that is to be measured as a medium.

The ultrasound image may be at least one selected from a B (brightness) mode image indicating a magnitude of an ultrasound echo signal reflected from an object as a brightness, a C (color) mode image indicating a speed of a moving object as a color by using a Doppler effect, a D (Doppler) mode image indicating an image of the moving object as a spectrum by using the Doppler effect, an M (motion) mode image indicating a motion of an object according to time in a predetermined position, and an E (elastic) mode image indicating a difference in a reaction between when compression is and is not applied to an object, as an image. However, the ultrasound image is not limited thereto. Also, the ultrasound image may be a two-dimensional image, a three-dimensional image, or a four-dimensional image. The ultrasound apparatus 1000 may obtain the ultrasound image by photographing an object. Also, the ultrasound apparatus 1000 may receive the ultrasound image from an external device.

The ultrasound apparatus 1000 may determine one from among a plurality of measuring devices, based on a user input selecting one from among the plurality of measuring devices for measuring the object in the ultrasound image. For example, the ultrasound apparatus 1000 may provide a measuring device selection menu for selecting one from among the plurality of measuring devices. The ultrasound apparatus 1000 may display the measuring device selection menu together with the ultrasound image on one screen. Also, the ultrasound apparatus 1000 may display the measuring device selection menu on a separate screen that is different from a touch screen on which the ultrasound image is displayed.

Also, the ultrasound apparatus 1000 may determine one from among the plurality of measuring devices, based on a user input selecting one from among a plurality of measurement items. The measurement item may include a length, a width, or an angle, but it is not limited thereto. When the ultrasound apparatus 1000 receives the user input selecting one measurement item, the ultrasound apparatus 1000 may determine a measuring device that is predetermined in correspondence to the selected measurement item.

Also, the ultrasound apparatus 1000 may determine one from among the plurality of measuring devices, based on a pattern of a user input. For example, when the ultrasound apparatus 1000 receives a user input touching two points on a touch screen and dragging the two points in opposite directions, the ultrasound apparatus 1000 may determine an oval measuring device as the measuring device. Also, when the ultrasound apparatus 1000 receives a user input touching two points on the touch screen and rotating one point, the ultrasound apparatus 1000 may determine a degree measuring device as the measuring device.

The ultrasound apparatus 1000 may display on the ultrasound image a measuring device image corresponding to the selected measuring device.

The measuring device image refers to a point that is to be measured in the ultrasound image, and may refer to an image medium of a graphic user interface for receiving a user input configuring a position of the measuring point. The measuring device image may be pre-stored in correspondence to the measuring device.

When the ultrasound apparatus 1000 determines one from among the plurality of measuring devices, the ultrasound apparatus 1000 may display a measuring device image corresponding to the determined measuring device, on the ultrasound image.

For example, when a vernier caliper measuring device is determined, the ultrasound apparatus 1000 may display a vernier caliper measuring device image on the ultrasound image. Also, when a pincette measuring device is determined, the ultrasound apparatus 1000 may display a pincette measuring device image on the ultrasound image. Also, when a scissors measuring device is determined, the ultrasound apparatus 1000 may display a scissors measuring device image on the ultrasound image.

The measuring device image may include a plurality of measuring points which indicate points on the ultrasound image that are to be measured. The points on the ultrasound image that are to be measured may be points in the ultrasound image, which is a reference for measurement. The measuring points on the ultrasound image may be configured by the user via the measuring device image. A position of the plurality of measuring points in the measuring device image may be pre-determined in correspondence to the measuring device image. For example, the plurality of measuring points in the measuring device image having a shape of the scissors, the plurality of measuring points may be both edges of the scissors.

Also, the measuring device image may include an adjusting portion for adjusting the position of the plurality of measuring points. Also, a position of the adjusting portion in the measuring device image may be pre-determined in correspondence to the measuring device image. For example, the adjusting portion in the measuring device image having the shape of the scissors may be a handle portion of the scissors.

The adjusting portion may be disposed not to overlap the plurality of measuring points in the measuring device image. For example, the adjusting portion may be apart from the plurality of measuring points in the measuring device image by a predetermined distance.

Also, the ultrasound apparatus 1000 may display the measuring device image such that the adjusting portion may be distinguished from other portions of the measuring device image. For example, the ultrasound apparatus 1000 may display the adjusting portion in a different color from other portions of the measuring device image.

The ultrasound apparatus 1000 may display the measuring device image half-transparently so that a portion of the ultrasound image, which overlaps the measuring device image, is not covered by the measuring device image.

The ultrasound apparatus 1000 may receive a touch input changing a position of the adjusting portion of the measuring device image on the ultrasound image, in operation S220.

The ultrasound apparatus 1000 may receive a touch and drag input with respect to the adjusting portion in the measuring device image. For example, the ultrasound apparatus 1000 may receive the input of touching the adjusting portion via a finger or an electronic pen, and dragging the finger or the electronic pen to another position in a screen, while maintaining the state of touching. When the ultrasound apparatus 1000 receives the touch and drag input, the ultrasound apparatus 1000 may move the adjusting portion along the drag.

In this case, the ultrasound apparatus 1000 may move the adjusting portion in the measuring device image by changing at least one of a position and a shape of the ultrasound image.

In operation S230, the ultrasound apparatus 1000 may adjust a position of at least one of the plurality of measuring points based on the changed position of the adjusting portion, and may obtain a measurement value based on a position of the plurality of measuring points including the at least one measuring point, the position of which is adjusted.

When the position of the adjusting portion is changed in the ultrasound image, the ultrasound apparatus 1000 may determine the position of the measuring point based on the position of the adjusting portion.

For example, the ultrasound apparatus 1000 may determine a point that is apart from a central point of the adjusting portion, by a pre-determined distance, as the measuring point. Also, the ultrasound apparatus 1000 may determine a point that is apart from a pre-determined adjusting point in the adjusting portion, by a pre-determined distance, along a direction of a straight line connecting the adjusting point and at least one reference point in the ultrasound image, as the measuring point. In this case, the ultrasound apparatus 1000 may adjust a position of at least one of the plurality of measuring points by changing at least one of a position and a shape of the measuring device image.

For example, the ultrasound apparatus 1000 may adjust the position of the at least one of the plurality of measuring points by adjusting a length of the measuring device image. Also, for example, the ultrasound apparatus 1000 may adjust the position of the at least one of the plurality of measuring points by rotating the measuring device image. Also, when the measuring device image is formed of two partial images crossing each other, based on a reference point, the ultrasound apparatus 1000 may adjust the position of the at least one of the plurality of measuring points by rotating the two partial images based on the reference point.

The ultrasound apparatus 1000 may obtain a measurement value with respect to a measurement item corresponding to a selected measuring device, based on the position of the plurality of measuring points.

When the position of the at least one of the plurality of measuring points is adjusted, the ultrasound apparatus 1000 may obtain the measurement value with respect to the measurement item corresponding to the selected measuring device, based on the position of the plurality of measuring points in the ultrasound image.

For example, the ultrasound apparatus 1000 may measure a distance between two measuring points on the ultrasound image, based on a position of the two measuring points on the measuring device image. The ultrasound apparatus 1000 may generate a circle having a straight line connecting the two measuring points as a diameter, based on the position of the measuring points, and may calculate at least one of the diameter, a circumferential length, and an area of the generated circle.

In this case, the ultrasound apparatus 1000 may convert a scale on the ultrasound image into a scale on a real object, in order to calculate a length, an area, and a volume.

Also, the ultrasound apparatus 1000 may configure an interest area on the ultrasound image based on the position of the plurality of measuring points and obtain a measurement value with respect to the configured interest area. For example, the ultrasound apparatus 1000 may configure a gate on the ultrasound image based on a position of two measuring points and measure a blood flow speed of an area indicated by the gate.

The ultrasound apparatus 1000 may display the obtained measurement value in operation S240.

The ultrasound apparatus 1000 may display the obtained measurement value on the measurement device image.

Also, the ultrasound apparatus 1000 may receive a touch input ending a touch and drag with respect to the adjusting portion. When receiving the touch input ending the touch and drag with respect to the adjusting portion, the ultrasound apparatus 1000 may display a button image for storing a measurement value, corresponding to the ultrasound image, on the ultrasound image.

Also, when receiving the touch input ending the touch and drag, the ultrasound apparatus 1000 may delete the measuring device image on the touch screen and may display a button image for re-adjusting the position of the plurality of measuring points, on the ultrasound image.

Figure 3:
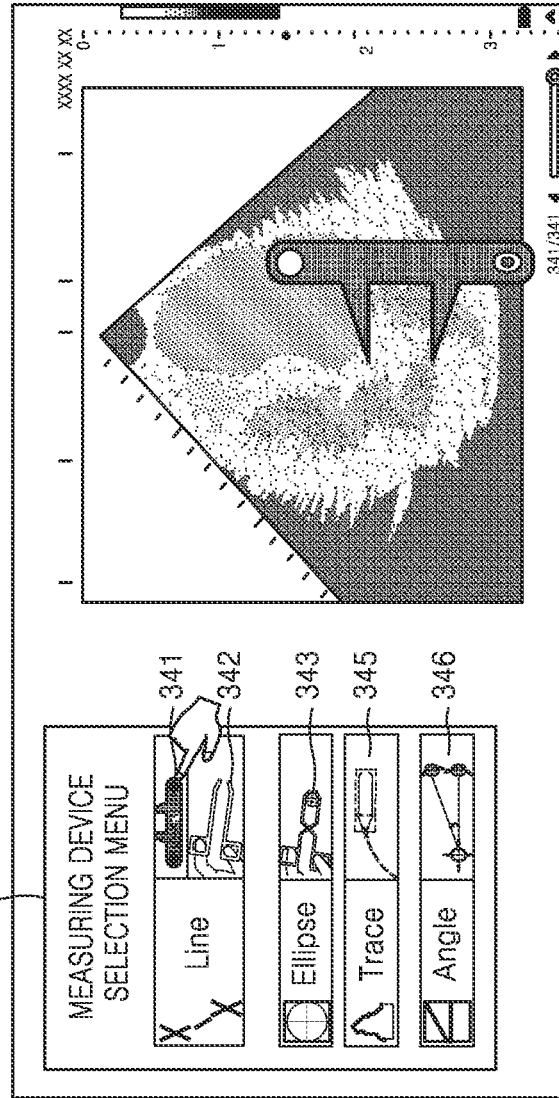
FIG. 3 is a view for describing a method of providing a measuring device selection menu via an ultrasound apparatus, according to an embodiment.

FIG. 3 is a view for describing a method of providing a measuring device selection menu 340 via the ultrasound apparatus 1000, according to an embodiment.

Referring to FIG. 3, the ultrasound apparatus 1000 may display the measuring device selection menu 340.

The measuring device selection menu 340 may include icons 341 through 346 for selecting a measuring device.

Also, the measuring device selection menu 340 may include information indicating shapes of an area measured by the measuring device. For example, the ultrasound apparatus 1000 may display a word 'line' indicating a distance, and an image indicating the distance, together with an icon for selecting a length measuring device.

Also, the measuring device selection menu 340 may include information indicating a measurement item measured by the measuring device. For example, the ultrasound apparatus 1000 may display a word 'angle' indicating an angle measured by the measuring device, and an angle image, together with an icon indicating an angle measuring device.

Also, when the ultrasound apparatus 1000 receives a user input selecting one from among the plurality of measuring devices, the ultrasound apparatus 1000 may display a measuring device image corresponding to the selected measuring device, on the ultrasound image. For example, when receiving a user input selecting the icon 341 for selecting a vernier caliper measuring device, the ultrasound apparatus 1000 may display a vernier caliper measuring device image corresponding to the vernier caliper measuring device, on the ultrasound image.

FIG. 3 illustrates a case in which the measuring device selection menu 340 includes the vernier caliper measuring device icon 341 corresponding to the vernier caliper measuring device for measuring a distance between a plurality of measuring points, a pincette measuring device icon 342 corresponding to a pincette measuring device, a scissors measuring device icon 343 corresponding to a scissors measuring device for measuring a measurement item with respect to an oval, a pen measuring device icon 345 corresponding to a pen measuring device for measuring an item with respect to a trace generated based on a user's touch trace, and an angle measuring device icon 346 corresponding to an angle measuring device. However, the measuring device may have other various shapes, and the measuring device selection menu 340 may include other measuring device icons corresponding to the measuring devices having various shapes.

FIG. 4 is a flowchart of a method of providing a measuring device via the ultrasound apparatus 1000, according to an embodiment.

The ultrasound apparatus 1000 may receive an input of selecting a vernier caliper measuring device, in operation S410.

The ultrasound apparatus 1000 may display a vernier caliper measuring device image, on an ultrasound image, in operation S420.

The ultrasound apparatus 1000 may display the vernier caliper measuring device image corresponding to the vernier caliper measuring device, on the ultrasound image.

The vernier caliper measuring device image may have a physical shape of a vernier caliper.

The vernier caliper measuring device image may include two measuring points which indicate positions of the two points in the ultrasound image that are to be measured. Also, the vernier caliper measuring device image may include an adjusting portion for adjusting the position of the measuring points.

The ultrasound apparatus 1000 may receive a touch input changing a position of the adjusting portion in the vernier caliper measuring device image, on the ultrasound image, in operation S430.

When the ultrasound apparatus 1000 receives a touch and drag input with respect to the adjusting portion, the ultrasound apparatus 1000 may move the adjusting portion along the dragged area. In this case, the ultrasound apparatus 1000 may move the adjusting portion by changing at least one of a shape and a position of the adjusting portion.

The ultrasound apparatus 1000 may determine a position of two measuring points that are apart from the adjusting portion by a pre-determined distance, based on the changed position of the adjusting portion, in operation S440.

When the at least one of the shape and the position of the adjusting portion is changed, the ultrasound apparatus 1000 may determine a position of a plurality of measuring points, based on the position of the adjusting portion.

For example, the ultrasound apparatus 1000 may determine a position of a measuring point based on a position of an adjusting point. The adjusting point may be a point in the measuring device image, which is becomes a reference point for determining the position of the measuring point. The position of the adjusting point may be a fixed point in the adjusting portion. For example, the position of the adjusting point may be a central point of the adjusting portion. The ultrasound apparatus 1000 may determine the position of the adjusting point based on the position of the adjusting portion.

When the ultrasound apparatus 1000 determines the position of the adjusting point, the ultrasound apparatus 1000 may determine a position of a point that is apart from a first adjusting point by a pre-determined distance and a position of a point that is apart from a second adjusting point by a pre-determined distance, the points apart from the first and second adjusting points being from among a plurality of points on a straight line connecting the first and second adjusting points, and then may determine points that are respectively apart from the determined positions by a pre-determined distance, along a direction perpendicular to the straight line, as the measuring point.

The ultrasound apparatus 1000 may adjust a position of at least one of two measuring points in the vernier caliper measuring device image, in operation S450.

The ultrasound apparatus 1000 may adjust the position of the at least one of the two measuring points, by changing at least one of a position and a shape of the vernier caliper measuring device image.

For example, the ultrasound apparatus 1000 may adjust the position of the at least one of the two measuring points, by rotating the vernier caliper measuring device image. Also, the ultrasound apparatus 1000 may adjust the position of the at least one of the two measuring points, by lengthening the vernier caliper measuring device image.

The ultrasound apparatus 1000 may calculate a distance between the two measuring points based on the determined position of the two measuring points, in operation S460.

The ultrasound apparatus 1000 may display the calculated distance, in operation S470.

Figure 5A:
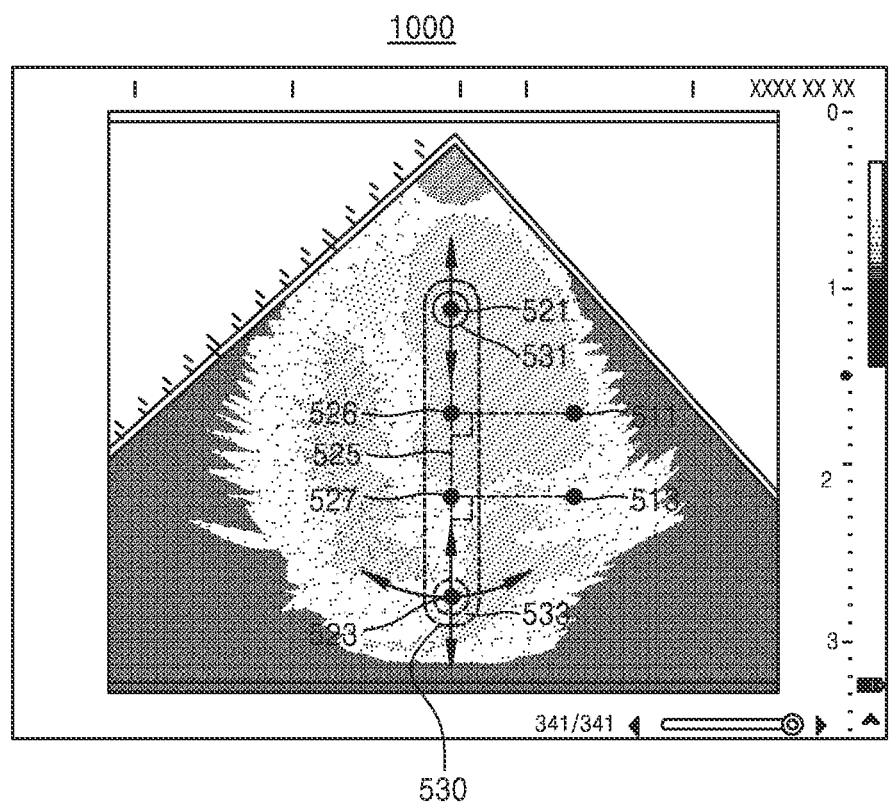
FIG. 5A is a view for describing a method of providing a distance measuring function via a vernier caliper measuring device, via an ultrasound apparatus, according to an embodiment.

FIG. 5A is a view for describing a method of providing a distance measuring function via a vernier caliper measuring device, via the ultrasound apparatus 1000, according to an embodiment.

Referring to FIG. 5A, when the vernier caliper measuring device is selected, the ultrasound apparatus 1000 may determine a measuring point and an adjusting portion on an ultrasound image.

For example, when receiving a user input selecting the icon 341 indicating the vernier caliper measuring device in the measuring device selection menu 340 illustrated in FIG. 3, the ultrasound apparatus 1000 may obtain a position of two measuring points 511 and 513 and the adjusting portion 530 on the ultrasound image. The adjusting portion 530 may include a first adjusting portion 531 and a second adjusting portion 533. A user may configure the measuring points 511 and 513 at a part that is to be measured in an object in the ultrasound image. For example, when the object is a fetus, and the measuring part is a nuchal translucency (NT) of the fetus, the user may locate the measuring points 511 and 531 at two end points of the NT. In this case, the user may move the first and second adjusting portions 531 and 533 to locate the measuring points 511 and 513 at the measuring part that is to be measured.

In detail, the measuring points 511 and 513 may be points on the ultrasound image, which is a reference for measurement. Also, the first and second adjusting portions 531 and 533 may be an area on the ultrasound image that receives a user's touch input for changing the location of the measuring points 511 and 513. Default locations of the two measuring points 511 and 513 and the adjusting portion 530 may be pre-determined in correspondence to the vernier caliper measuring device.

The vernier caliper measuring device may be a device for calculating a distance between the two measuring points 511 and 513. The ultrasound apparatus 1000 may calculate the distance between the two measuring points 511 and 513 based on the obtained location of the two measuring points 511 and 513.

When the ultrasound apparatus 1000 receives a touch and drag input with respect to the adjusting portion 530, the ultrasound apparatus 1000 may move the adjusting portion 530 along the dragged area. In this case, the ultrasound apparatus 1000 move the adjusting portion 530 by changing at least one of a shape and a position of the adjusting portion 530.

The first adjusting portion 531 may be configured to move above and below. Also, the second adjusting portion 533 may be configured to move above and below or to rotate based on a first adjusting point 521. Also, both of the adjusting portions 531 and 533 may simultaneously move in a parallel direction.

Other areas of the adjusting portion 530, except for the first adjusting portion 531 and the second adjusting portion 533, may be areas for the two measuring points 511 and 513 and the adjusting portion 530 to simultaneously move in the parallel direction.

When the adjusting portion 530 moves, the ultrasound apparatus 1000 may determine a position of the measuring points 511 and 513 based on the position of the adjusting portion 530. For example, the ultrasound apparatus 1000 may determine a position of adjusting points 521 and 523 based on a position of the first adjusting portion 531 and the second adjusting portion 533. The adjusting points 521 and 523 may be a point in the ultrasound image, which is becomes a reference point for determining the position of the measuring points 511 and 513. The position of the adjusting points 521 and 523 may be a central point of the first adjusting portion 531 and the second adjusting portion 533.

Also, when the position of the first adjusting portion 531 and the second adjusting portion 533 changes in the ultrasound image, the ultrasound apparatus 1000 may determine a position of a point 526 that is apart from the first adjusting point 521 by a pre-determined distance and a position of a point 527 that is apart from the second adjusting point 523 by a pre-determined distance, the points 526 and 527 apart from the first and second adjusting points 521 and 523 being from among a plurality of points on a straight line 525 connecting the first and second adjusting points 521 and 523, and then may determine the points 511 and 513 that are respectively apart from the determined positions 526 and 527 by a pre-determined distance, along a direction perpendicular to the straight line 525, as the measuring point. Accordingly, the measuring points 511 and 513 may be located at the position that is apart from the adjusting portions 531 and 533, by the pre-determined distance.

As illustrated in FIG. 5A, since the adjusting portion 530 is spaced apart from the measuring points 511 and 513, the measuring points 511 and 513 may be precisely configured without being covered by a finger, when the user configures the measuring points 511 and 513 by touching a random point in the adjusting portion 530 on a touch screen.

Also, when the position of the first adjusting portion 531 and the second adjusting portion 533 is changed in the ultrasound image, the ultrasound apparatus 1000 may store the changed position of the first adjusting portion 531 and the second adjusting portion 533 and the calculated position of the measuring points 511 and 513.

Figure 5B:
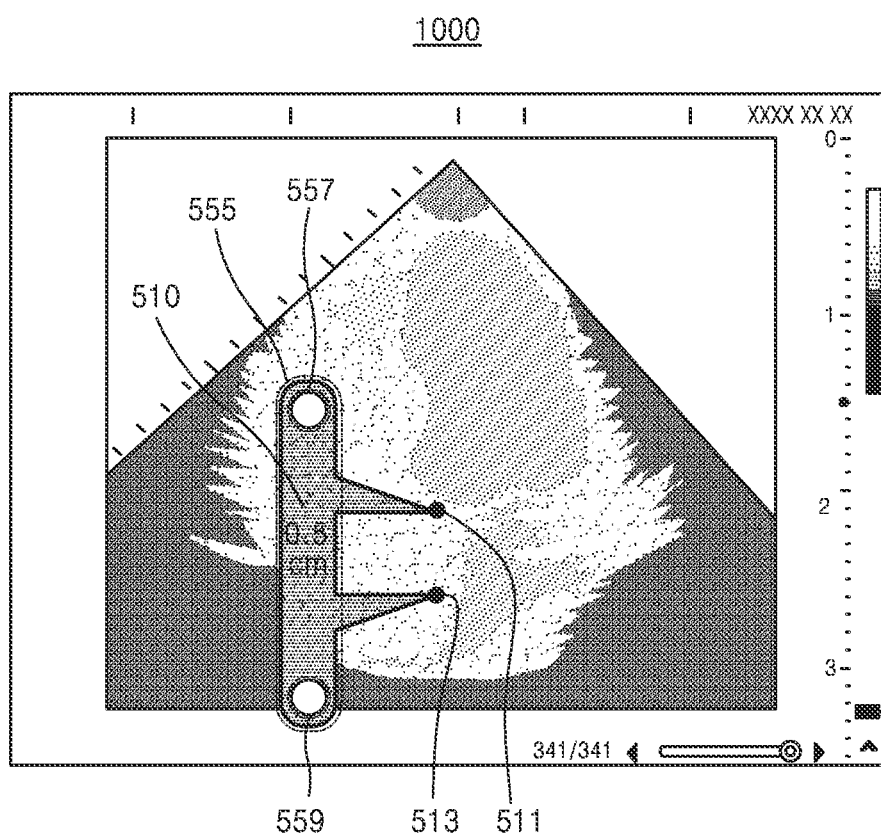
FIG. 5B is a view for describing a method of displaying a vernier caliper measuring device image corresponding to a vernier caliper measuring device, via an ultrasound apparatus, according to an embodiment.

FIG. 5B is a view for describing a method of displaying a vernier caliper measuring device image 510 corresponding to a vernier caliper measuring device via the ultrasound apparatus 1000, according to an embodiment.

Referring to FIG. 5B, when the vernier caliper measuring device is selected, the ultrasound apparatus 1000 may display the vernier caliper measuring device image 510 corresponding to the vernier caliper measuring device.

The vernier caliper measuring device image 510 may include two measuring points 511 and 513 which indicate two points in an ultrasound image that are to be measured. Also, the vernier caliper measuring device image 510 may include an adjusting portion 555 indicating an adjusting area. The adjusting portion 555 may include a first adjusting portion 557 indicating a position of a first adjusting area and a second adjusting portion 559 indicating a position of a second adjusting area.

The measuring points are located apart from the adjusting portion 555 by a pre-determined distance, and thus, the adjusting portion 555 indicating the adjusting area may be displayed at a location that is apart from the measuring points by the pre-determined distance.

The vernier caliper measuring device image 510 may have a physical shape of a vernier caliper. For example, the adjusting portion 555 may correspond to an area of a bar shape. Also, the two measuring points 511 and 513 may be located to be apart from the adjusting portion 555 by a pre-determined distance.

Also, when the adjusting portion 555 and the measuring points 511 and 513 are changed by a user's touch input, the ultrasound apparatus 1000 may change at least one of a position and a shape of the vernier caliper measuring device image 510 such that the adjusting portion 555 in the vernier caliper measuring device image 510 is located on the adjusting area and the two measuring points 511 and 513 indicate the measuring points.

Accordingly, a user may recognize a measuring point configured on the ultrasound image and a position of the adjusting area 530, from the vernier caliper measuring device image 510 displayed on the ultrasound image. Also, the ultrasound apparatus 1000 may receive a touch input with respect to the adjusting area 530, by receiving a touch input moving the adjusting portion 555 in the vernier caliper measuring device image 510. For example, the position of the first adjusting area may be moved along an area touched by the user. The ultrasound apparatus 1000 may receive a user's touch input moving the position of the first adjusting portion 557 by displaying the first adjusting portion 557 on the moved first adjusting area.

Figure 5C:
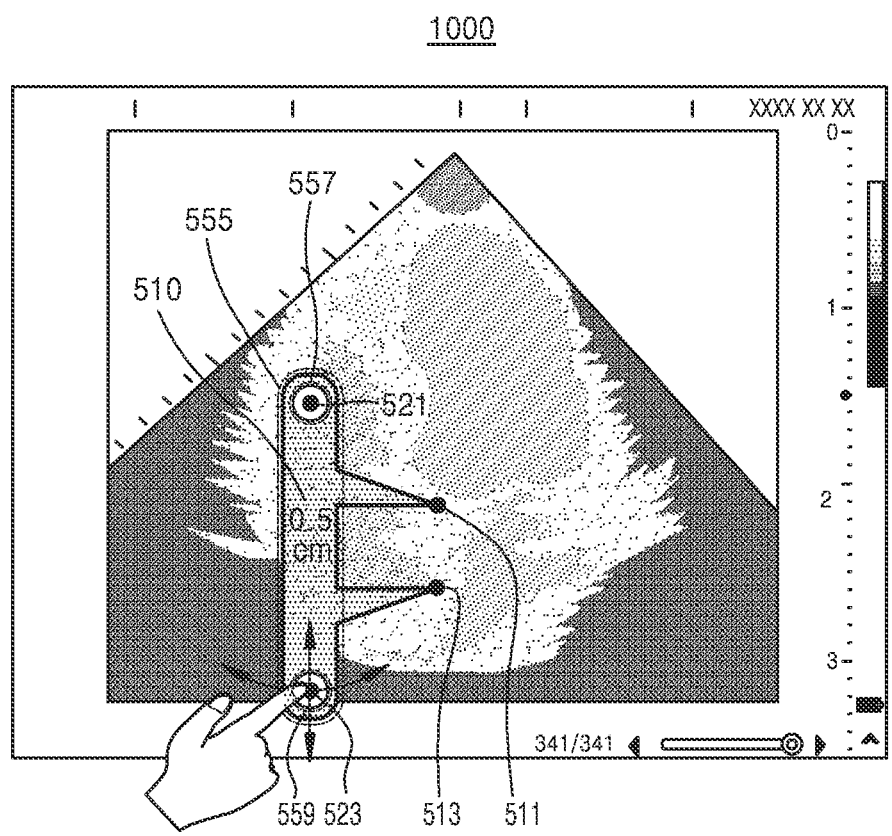
FIG. 5C is a view for describing a method of indicating a measuring point by changing a position or a shape of a vernier caliper measuring device image, according to an input of a user, via an ultrasound apparatus, according to an embodiment.

FIG. 5C is a view for describing a method of indicating a measuring point by changing a position or a shape of the vernier caliper measuring device image 510, according to a user input, via the ultrasound apparatus 1000, according to an embodiment.

Referring to FIG. 5C, the ultrasound apparatus 1000 may receive a touch input changing the position of the second adjusting portion 559. For example, the ultrasound apparatus 1000 may receive a touch input touching and dragging the second adjusting portion 559. When receiving the touch input touching and dragging the second adjusting portion 559, the ultrasound apparatus 1000 may adjust a position of two measuring points 511 and 513 in the ultrasound image by changing at least one of a position and a shape of the vernier caliper measuring device image 510.

For example, the ultrasound apparatus 1000 may receive the touch input rotating the second adjusting portion 559 based on the first adjusting point 521 that is the center of the first adjusting portion 557. When receiving the touch input rotating the second adjusting portion 559, the ultrasound apparatus 1000 may determine a position of the second adjusting point 523 based on the position of the second adjusting portion 559. When the position of the second adjusting point 523 is determined, the ultrasound apparatus 1000 may determine the position of the two measuring points 511 and 513, based on the first adjusting point 521 and the determined position of the second adjusting point 523.

Also, when receiving the touch input rotating the second adjusting portion 559, the ultrasound apparatus 1000 may rotate the vernier caliper measuring device image 510. When the vernier caliper measuring device image 510 is rotated, a point in the ultrasound image that is indicated by the measuring points 511 and 513 in the vernier caliper measuring device image 510 may be a point that is to be measured.

Also, for example, the ultrasound apparatus 1000 may receive a touch input reducing or increasing a length of the vernier caliper measuring device image 510. For example, the ultrasound apparatus 1000 may receive a touch input moving the second adjusting portion 559 in a lengthwise direction of the vernier caliper measuring device image 510. When receiving the touch input moving the second adjusting portion 559 in the lengthwise direction of the vernier caliper measuring device image 510, the ultrasound apparatus 1000 may determine the position of the second adjusting point 523, based on the position of the second adjusting portion 559. When the position of the second adjusting point 523 is determined, the ultrasound apparatus 1000 may determine the position of the second measuring point 513, based on the first adjusting point 521 and the determined position of the second adjusting point 523. Also, a distance between the first measuring point 511 and the second measuring point 513 may be calculated based on the first measuring point 511 and the determined position of the second measuring point 513.

Also, when receiving the touch input moving the second adjusting portion 559 in the lengthwise direction of the vernier caliper measuring device image 510, the length of the vernier caliper measuring device image 510 may be increased or decreased. When the length of the vernier caliper measuring device image 510 is increased or decreased, the point in the ultrasound image that is indicated by the measuring points 511 and 513 in the vernier caliper measuring device image 510 may be a point that is to be measured.

Figure 5D:
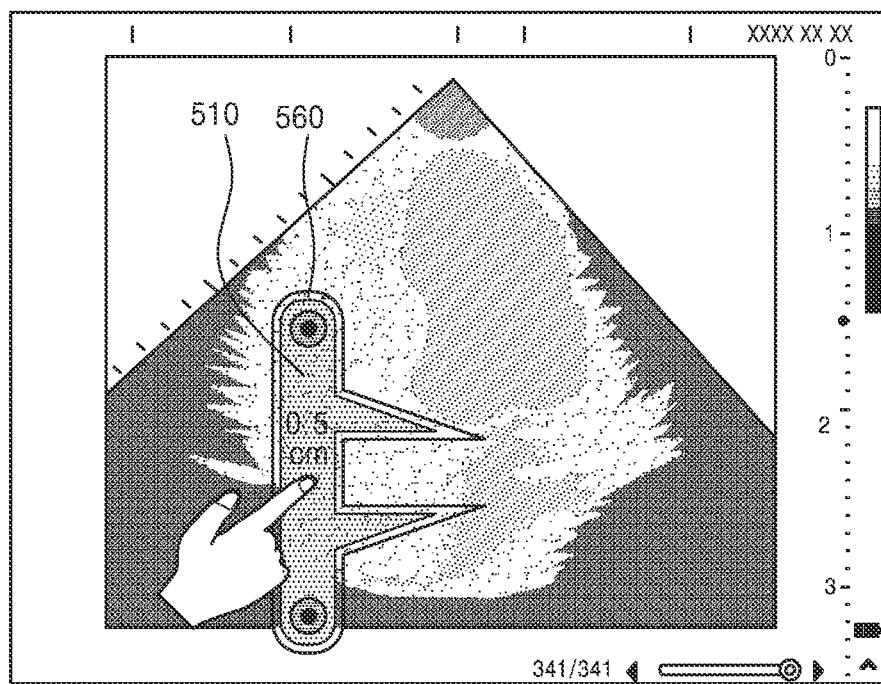
FIG. 5D is a view for describing a method of configuring a measuring point by changing a position of a vernier caliper measuring device image, according to an input of a user, via an ultrasound apparatus, according to another embodiment.

FIG. 5D is a view for describing a method of configuring a measuring point by changing a position of the vernier caliper measuring device image 510, according to a user input, via the ultrasound apparatus 1000, according to another embodiment.

Referring to FIG. 5D, the ultrasound apparatus 1000 may receive a touch input moving the entire vernier caliper measuring device image 510.

For example, the ultrasound apparatus 1000 may receive a user input touching other areas of the entire adjusting portion except for the first adjusting portion and the second adjusting portion. When the ultrasound apparatus 1000 receives the user input touching other areas of the entire adjusting portion except for the first adjusting portion and the second adjusting portion, the ultrasound apparatus 1000 may display an image 560 indicting that the entire vernier caliper measuring device image 510 is selected, on the vernier caliper measuring device image 510.

Also, when the ultrasound apparatus 1000 receives a touch input moving the entire vernier caliper measuring device image 510, the ultrasound apparatus 1000 may move the entire vernier caliper measuring device image 510. When the entire vernier caliper measuring device image 510 is moved, a point in the ultrasound image that is indicated by a measuring point in the vernier caliper measuring device image 510 may be a point that is to be measured.

Also, although it is not illustrated in FIG. 5D, the left and the right of the vernier caliper measuring device image 510 may be changed. For example, when the ultrasound apparatus 1000 receives a user input double-clicking the vernier caliper measuring device image 510, the ultrasound apparatus 1000 may display the vernier caliper measuring device image 510 changing the left and the right.

Figure 5E:
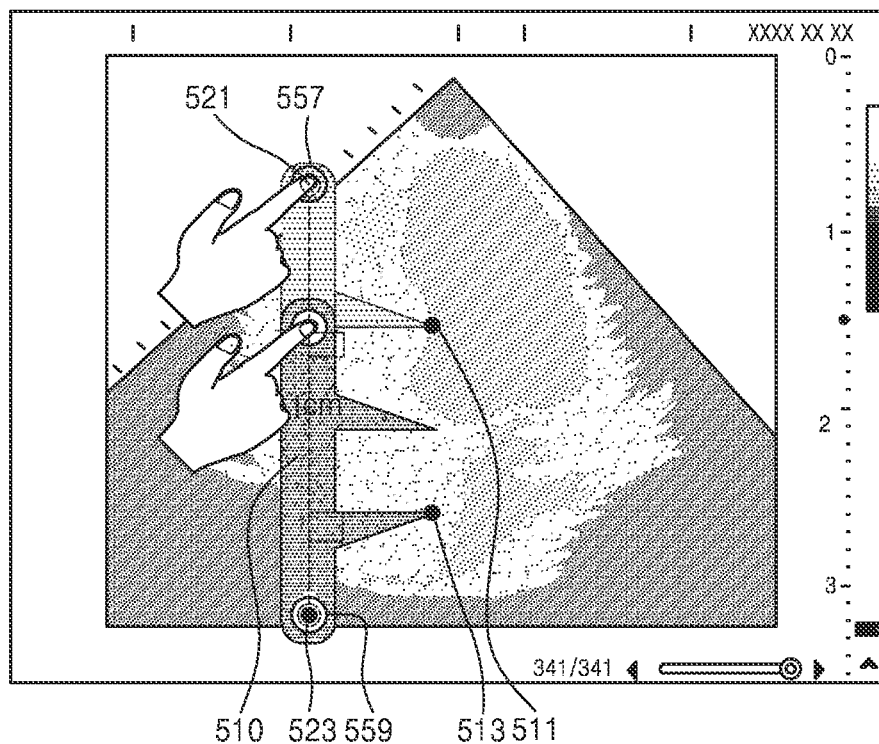
FIG. 5E is a view for describing a method of indicating a measuring point by changing a position or a shape of a vernier caliper measuring device image, according to an input of a user, via an ultrasound apparatus, according to another embodiment.

FIG. 5E is a view for describing a method of indicating a measuring point by changing a position or a shape of the vernier caliper measuring device image 510, according to a user input, via the ultrasound apparatus 1000, according to another embodiment.

Referring to FIG. 5E, the ultrasound apparatus 1000 may receive a touch input changing a position of the first adjusting portion 557. When receiving the input changing the position of the first adjusting portion 557, the ultrasound apparatus 1000 may adjust a position of the first measuring point 511 in an ultrasound image by changing at least one of the position and the shape of the vernier caliper measuring device image 510.

Also, the ultrasound apparatus 1000 may receive a touch input increasing or decreasing a length of the vernier caliper measuring device image 510. For example, the ultrasound apparatus 1000 may receive a touch input moving the first adjusting portion 557 in a lengthwise direction of the vernier caliper measuring device image 510. When receiving the touch input moving the first adjusting portion 557 in the lengthwise direction of the vernier caliper measuring device image 510, the ultrasound apparatus 1000 may determine the position of the first adjusting point 521, based on the position of the first adjusting portion 557. When the position of the first adjusting point 521 is determined, the ultrasound apparatus 1000 may determine the position of the first measuring point 511, based on the changed first adjusting point 521 and the second adjusting point 523. Also, a distance between the first measuring point 511 and the second measuring point 513 may be calculated based on the determined position of the first measuring point 511 and the second measuring point 513.

Also, when receiving the touch input moving the first adjusting portion 557 in the lengthwise direction of the vernier caliper measuring device image 510, the ultrasound apparatus 1000 may change the position of the first adjusting portion 557 by increasing or decreasing the length of the vernier caliper measuring device image 510. When the length of the vernier caliper measuring device image 510 is increased or decreased, the point in the ultrasound image that is indicated by the measuring points 511 and 513 in the vernier caliper measuring device image 510 may be a point that is to be measured.

Figure 6:
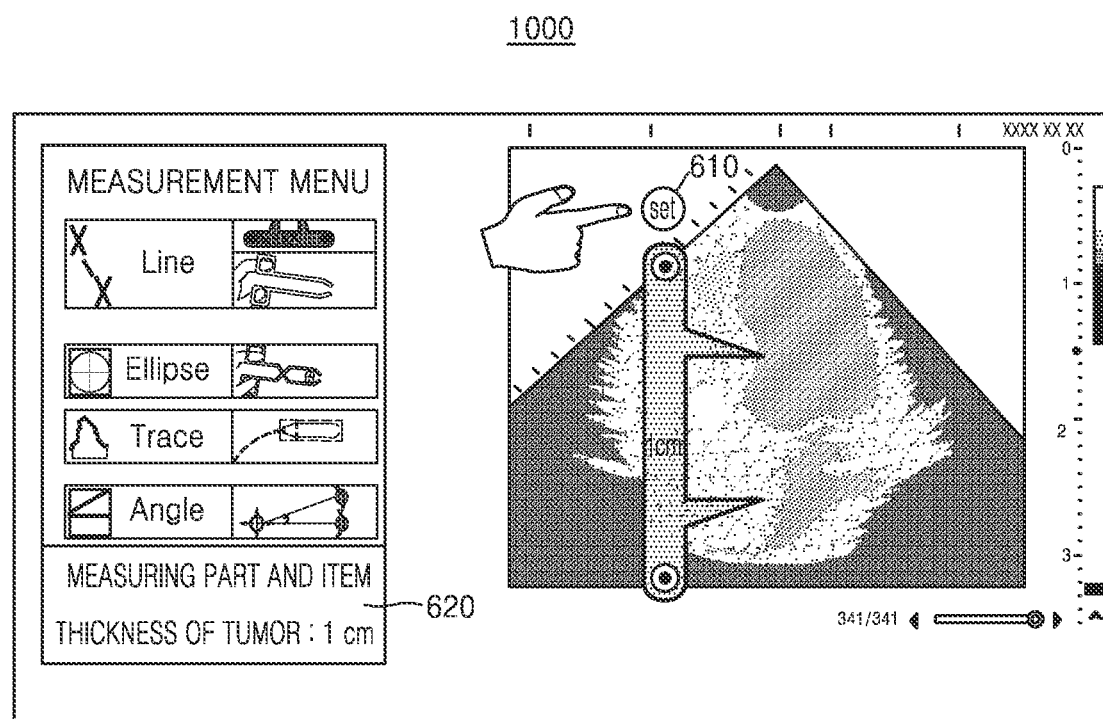
FIG. 6 is a view for describing a method of storing a calculated measurement value via an ultrasound apparatus, according to an embodiment.

FIG. 6 is a view for describing a method of storing a calculated measurement value via the ultrasound apparatus 1000, according to an embodiment.

Referring to FIG. 6, the ultrasound apparatus 1000 may display a button image for storing the calculated measurement value, on an ultrasound image.

For example, when the ultrasound apparatus 1000 receives a user input ending a touch and drag input with respect to an adjusting portion in a measuring device image, the ultrasound apparatus 1000 may display the button image for storing the calculated measurement value.

When receiving the input touching the button image for storing the calculated measurement value, the ultrasound apparatus 1000 may store the calculated measurement value in correspondence to identification information of the ultrasound image.

Also, when the user selects a measuring part and a measuring item 620 before selecting a measuring device, the ultrasound apparatus 1000 may display or store the calculated measurement value as a measurement value corresponding to the pre-selected measurement part and measurement item, when receiving the user input touching the icon for storing the measurement value.

Also, the ultrasound apparatus 1000 may store not only the measurement value but also a position of a measuring point and an adjusting area.

Figure 7A:
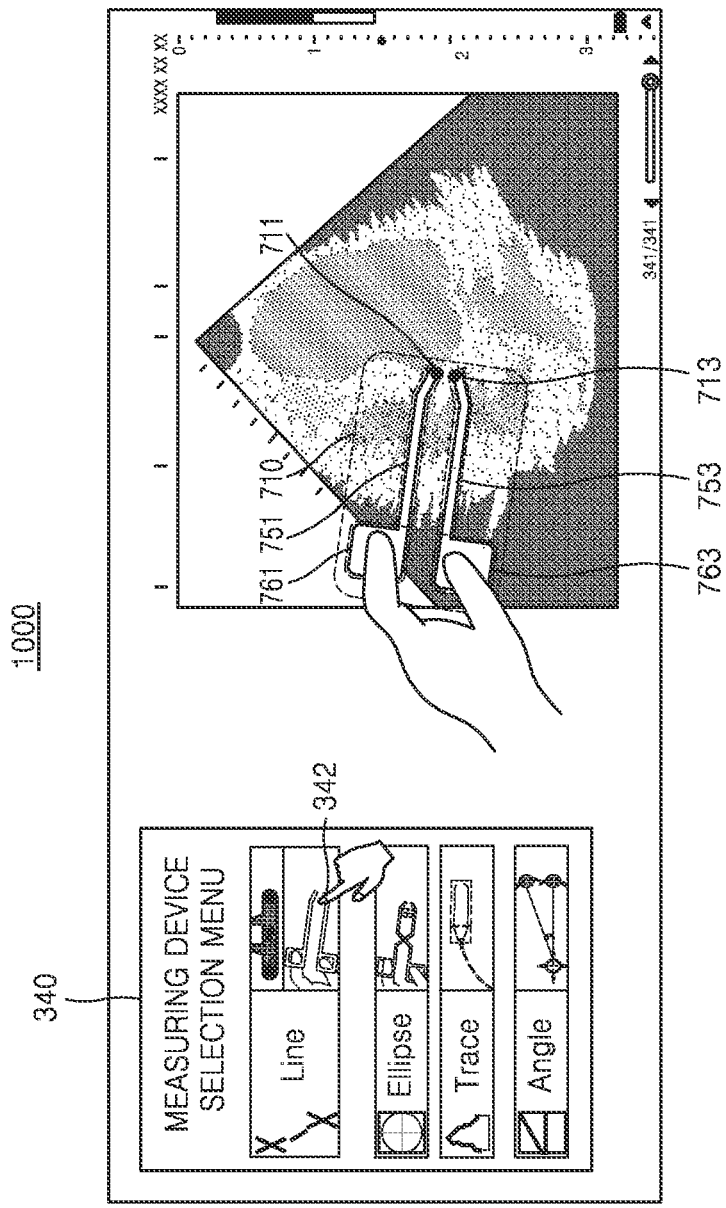
FIG. 7A is a view for describing a method of providing a distance measuring function via a pincette measuring device, via an ultrasound apparatus, according to an embodiment.

FIG. 7A is a view for describing a method of providing a distance measuring function via a pincette measuring device, via the ultrasound apparatus 1000, according to an embodiment.

Referring to FIG. 7A, the ultrasound apparatus 1000 may display a pincette measuring device image 710 on an ultrasound image.

When the ultrasound apparatus 1000 receives a user input selecting the pincette measuring device icon 342 in the measuring device selection menu 340, the ultrasound apparatus 1000 may display the pincette measuring device image 710 on the ultrasound image.

The pincette measuring device image 710 may have a physical shape of a pincette. Also, the pincette measuring device image 710 may be formed of two images.

The pincette measuring device image 710 may include two measuring points 751 and 753 which indicate two points in the ultrasound image that are to be measured. Also, the pincette measuring device image 710 may include two adjusting portions 761 and 763 for adjusting a position of the two measuring points 751 and 753.

The position of the measuring points 751 and 753 and the adjusting portions 761 and 763 may be pre-determined in the pincette measuring device image 710. For example, the measuring points 751 and 753 in the pincette measuring device image 710 may be a pincer portion of the pincette. Also, the adjusting portions 761 and 763 in the pincette measuring device image 710 may be a handle portion of the pincette.

The ultrasound apparatus 1000 may display the pincette measuring device image 710 such that the two measuring points 751 and 753 in the pincette measuring device image 710 indicate the two points in the ultrasound image that are to be measured, and the two adjusting portions 761 and 763 in the pincette measuring device image 710 are located in the adjusting area receiving a touch input of a user. Accordingly, the ultrasound apparatus 1000 may receive the user's touch input via the adjusting portions 761 and 763.

When receiving a user's touch input moving the adjusting portions 761 and 763 on the ultrasound image, the ultrasound apparatus 1000 may determine the position of the two measuring points on the ultrasound image, based on the changed position of the adjusting portions 761 and 763. For example, the ultrasound apparatus 1000 may determine a point that is apart from the adjusting portions 761 and 763 by a pre-determined distance as the two measuring points. In this case, the ultrasound apparatus 1000 may determine the two measuring points such that a straight line connecting the two measuring points is parallel to the adjusting portions 761 and 763.

Also, when receiving the user's touch input moving the adjusting portions 761 and 763 on the ultrasound image, the ultrasound apparatus 1000 may change at least one of a position and a shape of the pincette measuring device image 710 such that the measuring points 751 and 753 in the pincette measuring device image 710 indicate the points to be measured.

For example, when the ultrasound apparatus 1000 receives a touch input rotating the adjusting portions 761 and 763 in the same direction, the ultrasound apparatus 1000 may rotate the pincette measuring device image 710 based on a pre-determined point in the pincette measuring device image 710. Also, when receiving the touch input moving the adjusting portions 761 and 763, the ultrasound apparatus 1000 may move the entire pincette measuring device image 710 to another position in the ultrasound image. Also, when receiving a user input selecting the first adjusting portion 761 and the second adjusting portion 763 in the pincette measuring device image 710 and dragging the first and second adjusting portions 761 and 763 towards opposite directions, or towards a direction in which the first and second adjusting portions 761 and 763 get near to each other, the ultrasound apparatus 1000 may perform a parallel displacement of the two images respectively corresponding to two pincers in opposite directions or in a direction in which the two images get near to each other. Also, the ultrasound apparatus 1000 may adjust a length of the pincette measuring device image 710 based on a pre-determined point in the pincette measuring device image 710.

Figure 7B:
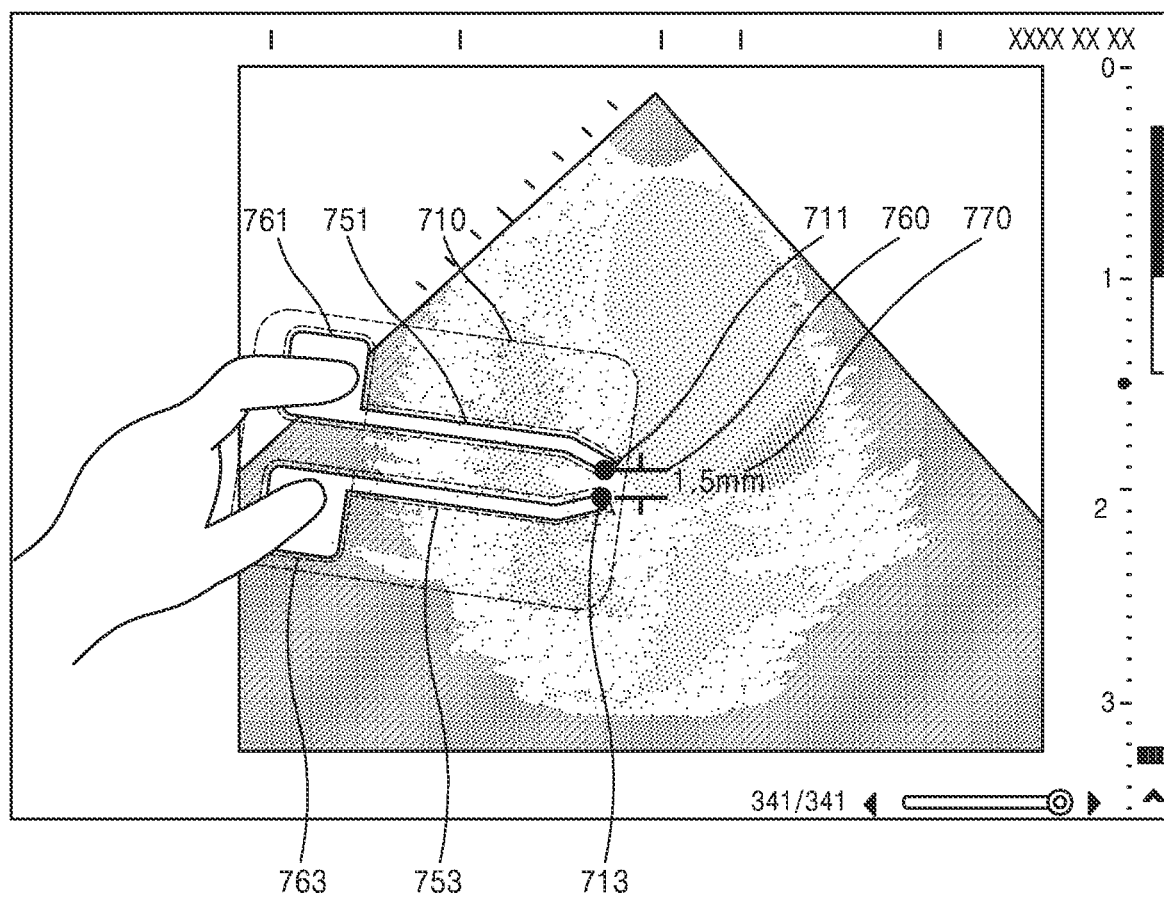
FIG. 7B is a view for describing a method of providing a pincette measuring device, via an ultrasound apparatus, according to another embodiment.

FIG. 7B is a view for describing a method of providing a pincette measuring device via the ultrasound apparatus 1000, according to another embodiment.

Referring to FIG. 7B, the ultrasound apparatus 1000 may display a measurement value obtained via the pincette measuring device image 710.

When the ultrasound apparatus 1000 receives a user's touch input moving the adjusting portions 761 and 763 on an ultrasound image, the ultrasound apparatus 1000 may determine a position of measuring points 711 and 713 and may calculate a distance between the measuring points 711 and 713 based on the determined position. Also, the ultrasound apparatus 1000 may display information 770 of the calculated distance on the ultrasound image.

Also, the ultrasound apparatus 1000 may display an image 760 indicating a position and a range of a measured area, on the ultrasound image.

Also, the ultrasound apparatus 1000 may configure the measured area as an interest area and may display interest information with respect to the configured interest area. For example, the ultrasound apparatus 1000 may configure the measured area as a simple volume. Also, the ultrasound apparatus 1000 may display information of a blood flow at a part indicated by the configured sample volume as a spectrum. Accordingly, the user may adjust a length of the sample volume via the pincette measuring device image 710.

Figure 8:
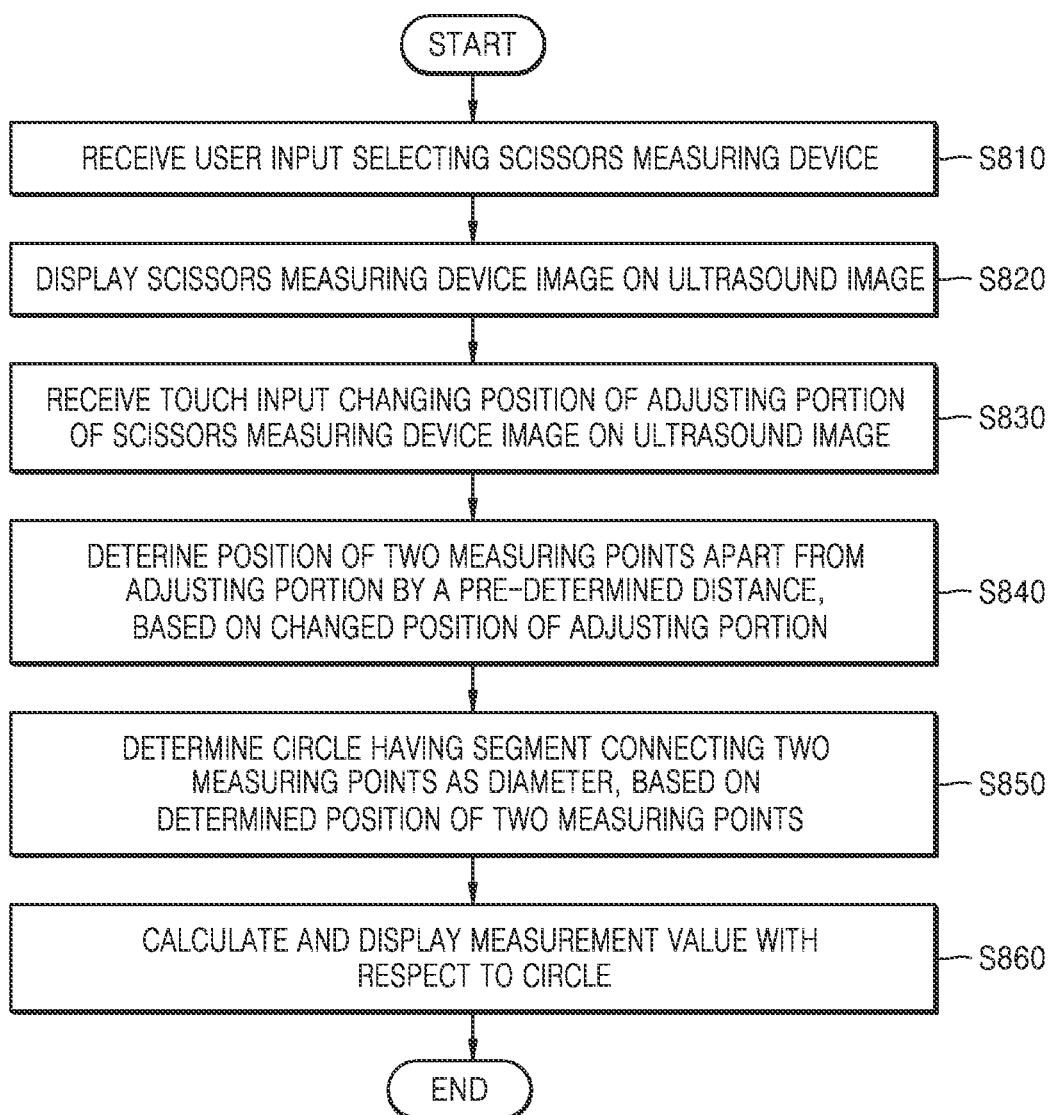
FIG. 8 is a flowchart of a method of providing a measuring function via a scissors measuring device, via an ultrasound apparatus, according to an embodiment.

FIG. 8 is a flowchart of a method of providing a measuring function via a scissors measuring device, via the ultrasound apparatus 1000, according to an embodiment.

The ultrasound apparatus 1000 may receive a user input selecting the scissors measuring device, in operation S810.

The ultrasound apparatus 1000 may display a scissors measuring device image on an ultrasound image, in operation S820.

The ultrasound apparatus 1000 may display the scissors measuring device image corresponding to the scissors measuring device on the ultrasound image.

The scissors measuring device image may have a physical shape of the scissors.

The scissors measuring device image may include two measuring points, which indicate two points in the ultrasound image that are to be measured. The measuring points may be a point on the ultrasound image, which becomes a reference point for measurement. The plurality of measuring points in the scissors measuring device image having the physical shape of the scissors may be end points at both edges of the scissors.

Also, the scissors measuring device image may include an adjusting portion indicating an adjusting area. Also, the adjusting area may be an area on the ultrasound image for receiving a user's touch input for changing a position of the measuring points. Also, in the scissors measuring device image having a shape of the scissors, the adjusting portion may be a handle portion of the scissors.

Also, the adjusting portion and the measuring point may be disposed to be apart from each other in the measuring device image. For example, the adjusting portion may be disposed not to overlap the measuring point in the measuring device image. Also, for example, the adjusting portion may be disposed in an area that is apart from the measuring point by a pre-determined distance, in the measuring device image.

The ultrasound apparatus 1000 may receive a touch input changing a position of the adjusting portion of the scissors measuring device image, on the ultrasound image, in operation S830.

When receiving a touch and drag input with respect to the adjusting portion, the ultrasound apparatus 1000 may move the adjusting portion along the dragged area. In this case, the ultrasound apparatus 1000 may move the adjusting portion by changing at least one of a shape and a position of the adjusting portion.

The ultrasound apparatus 1000 may determine a position of two measuring points that are apart from the adjusting portion by a pre-determined distance, based on the changed position of the adjusting portion, in operation S840.

When the at least one of the shape and the position of the adjusting portion is changed, the ultrasound apparatus 1000 may determine a position of the plurality of measuring points, based on the position of the adjusting portion.

For example, the ultrasound apparatus 1000 may determine a position of an adjusting point based on the position of the adjusting portion. The adjusting point may be a point in the measuring device image, which is a reference point for determining the position of the measuring point. The adjusting point may be a fixed point in the adjusting portion.

When the position of the adjusting point is determined, the ultrasound apparatus 1000 may determine a point that is apart from the adjusting point by a pre-determined distance along a direction of a straight line connecting the adjusting point and at least one reference point determined on the ultrasound image, as the measuring point.

The ultrasound apparatus 1000 may adjust the position of the adjusting portion and two measuring points by changing at least one of a position and a shape of the scissors measuring device image. For example, when an area indicating a handle of the scissors is moved, the ultrasound apparatus 1000 may change the scissors measuring device image as a shape in which both edges of the scissors are closed or a shape in which both edges of the scissors are open, such that ends of the both edges of the scissors indicate the points in the ultrasound image that are to be measured.

The ultrasound apparatus 1000 may determine a circle having a segment connecting the two measuring points as a diameter, based on the determined position of the two measuring points, in operation S850.

The ultrasound apparatus 1000 may calculate and display a measurement value with respect to the circle, in operation S860.

The ultrasound apparatus 1000 may calculate at least one of a diameter, a circumferential length, and an area of the circle.

Figure 9A:
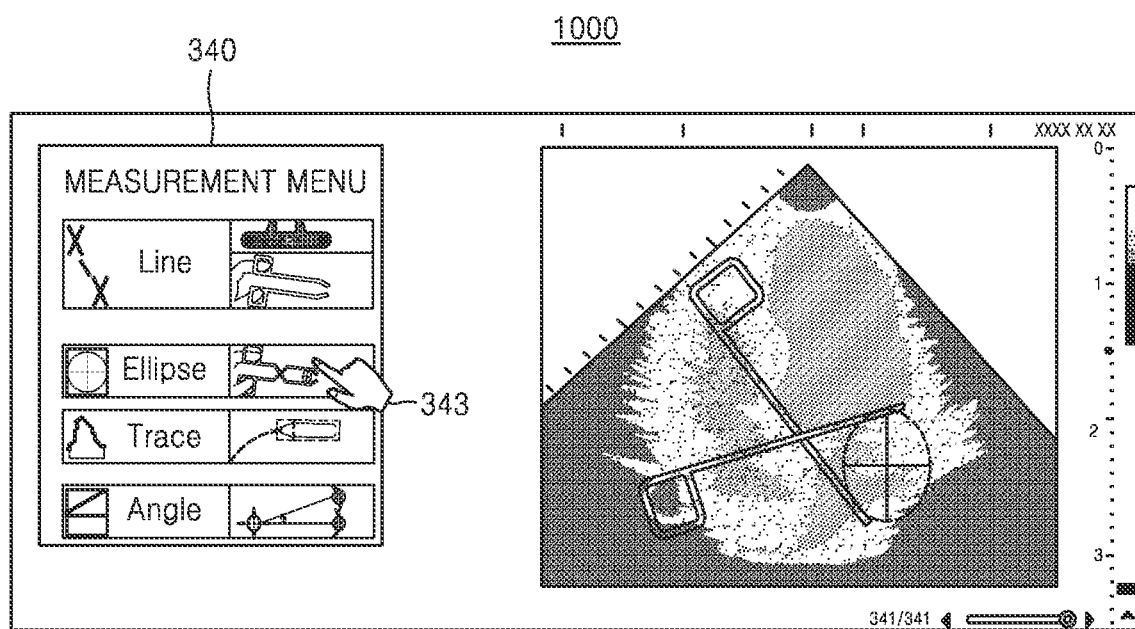
FIG. 9A is a view for describing a method of providing a measuring function via a scissors measuring device, via an ultrasound apparatus, according to an embodiment.

FIG. 9A is a view for describing a method of providing a measuring function via a scissors measuring device, via the ultrasound apparatus 1000, according to an embodiment.

Referring to FIG. 9A, the ultrasound apparatus 100 may display a scissors measuring device image on an ultrasound image.

When the ultrasound apparatus 1000 receives a user input selecting the icon 343 indicating the scissors measuring device, the ultrasound apparatus 1000 may display the scissors measuring device image corresponding to the scissors measuring device, on the ultrasound image.

Figure 9B:
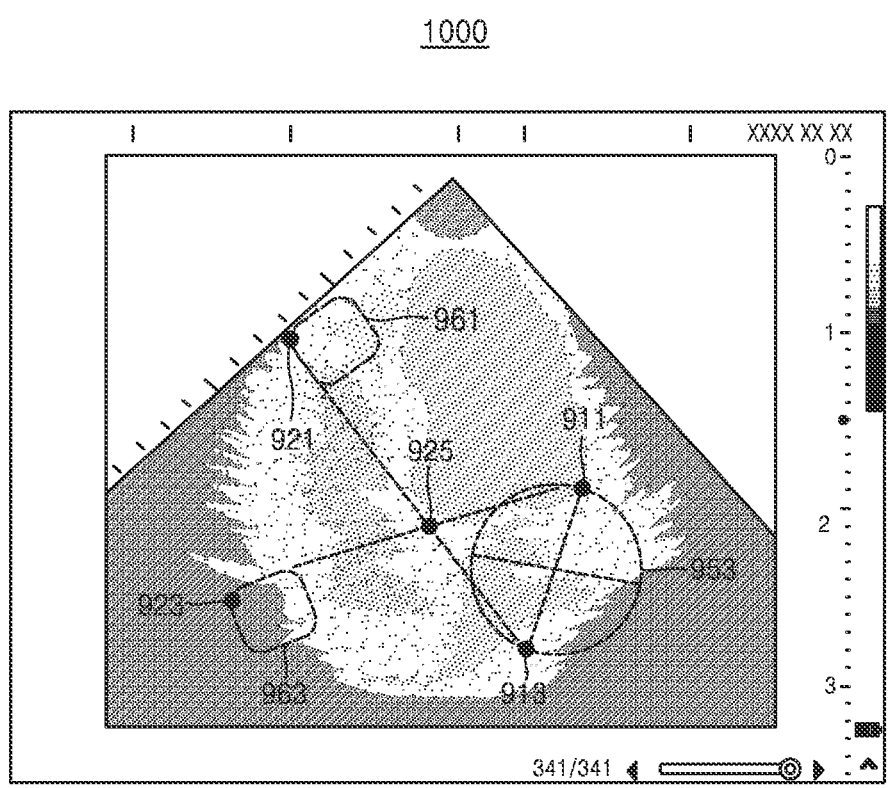
FIG. 9B is a view for describing a method of obtaining measurement information with respect to a circle via a scissors measuring device, via an ultrasound apparatus, according to an embodiment.

FIG. 9B is a view for describing a method of obtaining a measurement value with respect to a circle via the scissors measuring device, via the ultrasound apparatus 1000, according to an embodiment.

When the ultrasound apparatus 1000 receives a user input selecting the scissors measuring device, the ultrasound apparatus 1000 may obtain a position of two measuring points 911 and 913 and two adjusting areas 961 and 963, corresponding to the scissors measuring device, on the ultrasound image. The measuring points may be points on the ultrasound image that is a reference point for measurement. Also, the adjusting areas may be areas on the ultrasound image that receive a user's touch input for changing the position of the measuring points. A default location of the two measuring points 911 and 913 and the two adjusting areas 961 and 963 may be pre-determined in correspondence to the scissors measuring device.

The scissors measuring device may be a device for measuring a diameter, a circumferential length, and an area of a circle area 953 having a straight line 951 connecting the two measuring points 911 and 913 as the diameter. The ultrasound apparatus 1000 may determine the circle area 953 based on the obtained position of the two measuring points 911 and 913. Also, the ultrasound apparatus 1000 may calculate the diameter, the circumferential length, and the area of the circle area 953 based on the obtained position of the measuring points 911 and 913.

When receiving a touch and drag input with respect to the adjusting areas 961 and 963, the ultrasound apparatus 1000 may move the adjusting areas 961 and 963 along the dragged area. In this case, the ultrasound apparatus 1000 may move the adjusting areas 961 and 963 by changing the position of the adjusting areas 961 and 963.

Also, when the position of the adjusting areas is changed by the user's input, the ultrasound apparatus 1000 may determine the position of the measuring points 911 and 913, based on the position of the adjusting areas 961 and 963.

For example, the ultrasound apparatus 1000 may determine a position of two adjusting points 921 and 923, based on the position of the first adjusting area 961 and the second adjusting area 963. The position of the two adjusting points 921 and 923 may be pre-determined in the adjusting areas 961 and 963. The two adjusting points 921 and 923 may include the first adjusting point 921 in the first adjusting area 961 and the second adjusting point 923 in the second adjusting area 963.

The ultrasound apparatus 1000 may determine a cross point 925 of straight lines connecting the two adjusting points 921 and 923 and the pre-stored two measuring points 911 and 913. The cross point 925 may be a reference point for a movement of the first adjusting area 961 and the second adjusting area 963.

When the ultrasound apparatus 1000 receives a user input rotating the first adjusting area 961 or the second adjusting area 963 based on the cross point 925, the ultrasound apparatus 1000 may rotate the first adjusting point 921 and the second adjusting point 923 based on the cross point 925. When the second adjusting point 923 rotates based on the cross point 925, the ultrasound apparatus 1000 may determine, based on the changed position of the second adjusting point 923, a point that is apart from the second adjusting point 923 by a pre-determined distance, along a direction of the straight line connecting the second adjusting point 923 and the cross point 925, as the first measuring point 911. Also, when the first adjusting point 921 rotates based on the cross point 925, the ultrasound apparatus 1000 may determine, based on the changed position of the first adjusting point 921, a point that is apart from the first adjusting point 921 by a pre-determined distance, along a direction of the straight line connecting the first adjusting point 921 and the cross point 925, as the second measuring point 913.

Also, when the position of the first adjusting area 961 and the second adjusting area 963 in the ultrasound image is changed, the ultrasound apparatus 100 may store the changed position of the first adjusting area 961 and the second adjusting area 963, and the determined position of the measuring points 911 and 913.

The first adjusting area 961 and the second adjusting area 963 may be configured to be rotatable based on the cross point 925. Also, the touch input with respect to the first adjusting area 961 and the second adjusting area 963 may be simultaneously received. Accordingly, the ultrasound apparatus 1000 may simultaneously change the two measuring points 911 and 913, by receiving two-touch inputs.

Also, when the ultrasound apparatus 1000 receives a long touch input with respect to the first adjusting area 961 and the second adjusting area 963, and a touch input moving the first adjusting area 961 and the second adjusting area 963, the ultrasound apparatus 1000 may simultaneously move the first adjusting area 961, the second adjusting area 963, and the cross point 925, along a parallel direction.

Also, when the ultrasound apparatus 1000 receives a long touch input with respect to the first adjusting area 961 and the second adjusting area 963, and a touch input rotating the first adjusting area 961 and the second adjusting area 963, the ultrasound apparatus 1000 may simultaneously rotate the first adjusting area 961, the second adjusting area 963, and the cross point 925.

Also, when the ultrasound apparatus 1000 receives a touch input with respect to the cross point 925, and a touch input moving the cross point 925, the ultrasound apparatus 1000 may move the position of the measuring points 911 and 913 based on the adjusting points 921 and 923 and the moved cross point 925. For example, when receiving the touch input moving the cross point 925 such that the cross point 925 gets near the adjusting points 921 and 923, the ultrasound apparatus 1000 may determine the position of the measuring points 911 and 913 based on the adjusting points 921 and 923 and the moved cross point 925. In this case, the measuring points 911 and 913 may be distanced apart from each other. Also, when receiving the touch input moving the cross point 925 such that the cross point 925 gets far from the adjusting points 921 and 923, the ultrasound apparatus 1000 may determine the position of the measuring points 911 and 913 based on the adjusting points 921 and 923 and the moved cross point 925. In this case, the measuring points 911 and 913 may get near to each other.

Figure 9C:
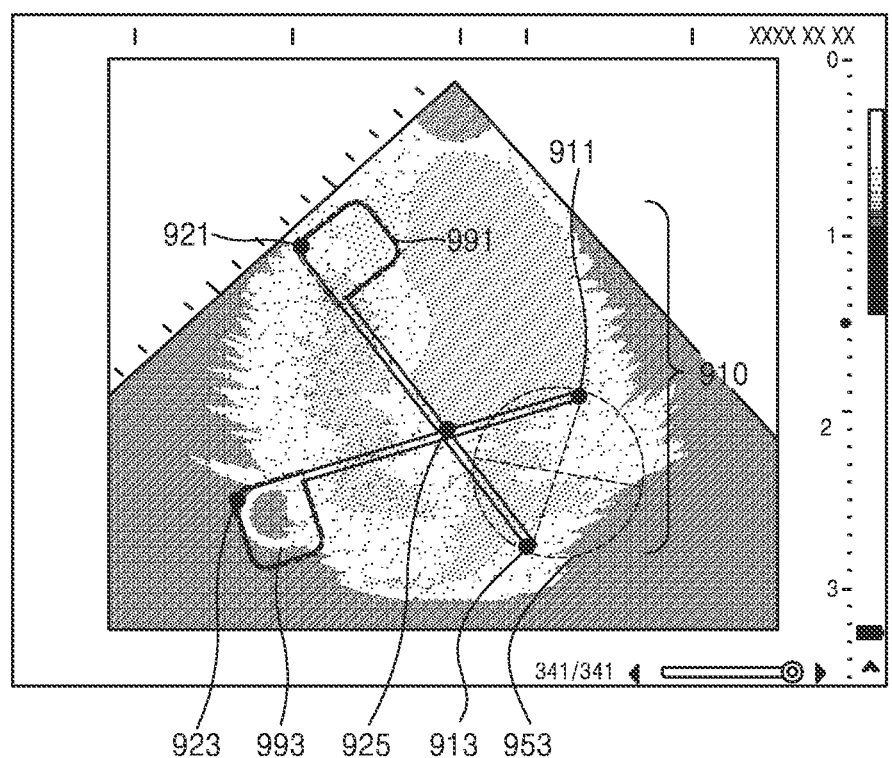
FIG. 9C is a view for describing a method of displaying a measuring device image corresponding to a scissors measuring device, via an ultrasound apparatus, according to an embodiment.

FIG. 9C is a view for describing a method of displaying a measuring device image 910 corresponding to a scissors measuring device, via the ultrasound apparatus 100, according to an embodiment.

Referring to FIG. 9C, when the scissors measuring device is selected, the ultrasound apparatus 1000 may display the measuring device image 910 corresponding to the scissors measuring device.

The measuring device image 910 corresponding to the scissors measuring device may include two measuring points 911 and 913 which indicate points in an ultrasound image that are to be measured. Also, the measuring device image 910 corresponding to the scissors measuring device may include two adjusting portions 991 and 993 which indicate adjusting areas. Also, the measuring device image 910 may display an image 953 indicating a circle having the two measuring points 911 and 913 as a diameter.

The measuring device image 910 corresponding to the scissors measuring device may have a physical shape of the scissors. Also, a position of the two measuring points 911 and 913 and the two adjusting portions 991 and 993 may be pre-determined in the scissors measuring device image 910. For example, the two measuring points 911 and 913 may be ends of both edges of the scissors of the scissors measuring device image 910. Also, the two adjusting portions 991 and 993 may be a handle portion of the scissors of the scissors measuring device image 910.

The ultrasound apparatus 1000 may display the scissors measuring device image 910 such that the two measuring points 911 and 913 in the scissors measuring device image 910 indicate two points in the ultrasound image that are to be measured, and a cross point of the both edges of the scissors is located at the cross point 925 of FIG. 9B. Accordingly, the measuring device image 910 may have a shape in which two partial images cross each other based on the cross point.

Also, the ultrasound apparatus 1000 may receive a touch input with respect to adjusting areas, by receiving a touch input moving the adjusting portions 991 and 993 in the measuring device image 910. For example, the ultrasound apparatus 1000 may move a position of the first adjusting area along the touched area. Also, the ultrasound apparatus 1000 may receive a user's touch input moving a position of the first adjusting portion 991, by displaying the first adjusting portion 991 on the moved position of the first adjusting area. Accordingly, the user may recognize the position of the measuring points and the adjusting areas configured on the ultrasound image, from the measuring device image 910 displayed on the ultrasound image.

Figure 9D:
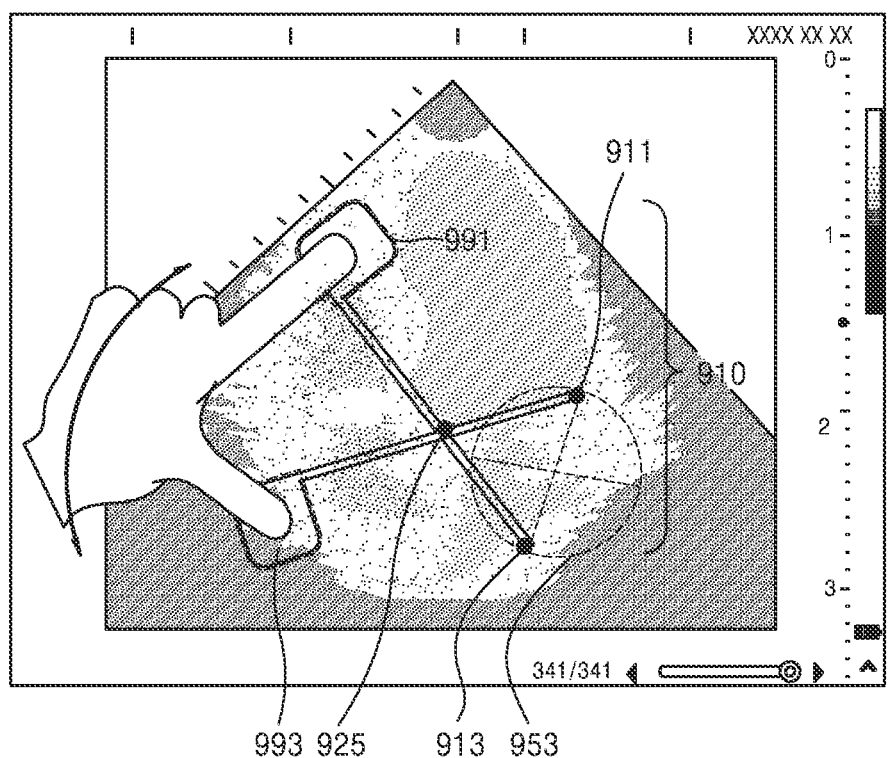
FIG. 9D is a view for describing a method of indicating a measuring point by changing a position or a shape of a measuring device image, according to an input of a user, via an ultrasound apparatus, according to an embodiment.

FIG. 9D is a view for describing a method of indicating a measuring point by changing a position or a shape of the measuring device image 510, according to an input of a user, via the ultrasound apparatus 1000, according to an embodiment.

Referring to FIG. 9D, the ultrasound apparatus 1000 may receive a touch input changing the position of the adjusting portions 991 and 993. When receiving the touch input changing the position of the adjusting portions 991 and 993, the ultrasound apparatus 1000 may adjust the position of the two measuring points 911 and 913 in the ultrasound image, by changing at least one of a position and a shape of the measuring device image 910.

For example, when the ultrasound apparatus 1000 receives a touch input rotating the adjusting portions 991 and 993 such that the adjusting portions 991 and 993 get far from each other in opposite directions or near to each other in the same direction, the ultrasound apparatus 1000 may determine the position of the two measuring points 911 and 913 based on the changed position of the adjusting portions 991 and 993 and the position of the cross point 925.

Also, when receiving the touch input rotating the adjusting portions 991 and 993 such that the adjusting portions 991 and 993 get far from each other in opposite directions or near to each other in the same direction, the ultrasound apparatus 1000 may rotate two partial images based on the cross point 925. For example, the ultrasound apparatus 1000 may rotate the both edges of the scissors in the scissors measuring device image 910, based on the cross point 925. In this case, the speed and angle of the rotation may be determined based on a speed and a distance at which the adjusting portions 991 and 993 get far from each other in opposite directions. When the two partial images rotate, the point in the ultrasound image that is indicated by the measuring points 911 and 913 in the measuring device image 910 may be a point that is to be measured.

Also, when the position of the measuring points 911 and 913 is determined, the ultrasound apparatus 1000 may determine a circle having a straight line formed by the two measuring points 911 and 913 as a diameter. Also, the ultrasound apparatus 1000 may display the image 953 indicating a circle at the determined position of the circle. Also, the ultrasound apparatus 1000 may calculate at least one of a length of a diameter, a circumferential length, and an area of the determine circle.

Also, when the ultrasound apparatus 1000 receives two touch inputs with respect to the adjusting portions 991 and 993, the ultrasound apparatus 1000 may simultaneously rotate the two partial images based on the cross point 925.

Also, when the ultrasound apparatus 1000 receives a long touch input with respect to the first adjusting portion 991 and the second adjusting portion 993 and a touch input moving the first adjusting portion 991 and the second adjusting portion 993, the ultrasound apparatus 1000 may move the entire scissors measuring device image 910.

Also, when the ultrasound apparatus 1000 receives a long touch input with respect to the first adjusting portion 991 and the second adjusting portion 993 and a touch input rotating the first adjusting portion 991 and the second adjusting portion 993, the ultrasound apparatus 100 may rotate the entire scissors measuring device image 910.

Figure 10A:
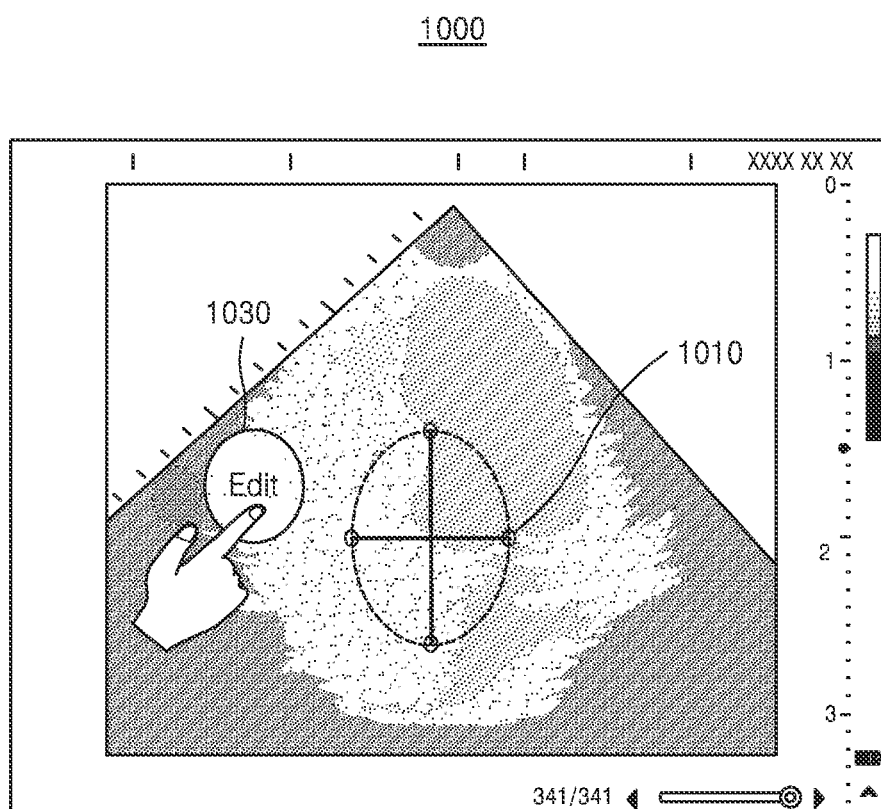
FIG. 10A is a view for describing a method of providing a measuring function in a direct change mode, via an ultrasound apparatus, according to another embodiment.

FIG. 10A is a view for describing a method of providing a measuring function in a direct change mode, via the ultrasound apparatus 1000, according to another embodiment.

Referring to FIG. 10A, the ultrasound apparatus 1000 may display a button image 1030 for entering into the direct change mode in which a configured measuring area may be changed without using a measuring device image.

When a user's touch input with respect to the measuring device image is ended, the ultrasound apparatus 1000 may display the button image 1030 for entering into the direct change mode. In this case, the ultrasound apparatus 1000 may also display a button image for storing a measurement value. Also, when receiving a user input double touching an area of the ultrasound image, in which the measuring device image is not displayed, the ultrasound apparatus 1000 may display the button image 1030 for entering into the direct change mode.

When receiving the user input touching the button image 1030 for entering into the direct change mode, the ultrasound apparatus 1000 may delete the measuring device image and display the image 1010 indicating a configured measuring area.

Also, when the ultrasound apparatus 1000 enters into the direct change mode, the ultrasound apparatus 1000 may display an image indicating that the direct change mode is entered into. For example, the ultrasound apparatus 1000 may change a size or a color of the image 1010 indicating the measuring area. Also, the ultrasound apparatus 1000 may display a handle image indicating the adjusting portions in the image 1010 indicating the measuring area, on the adjusting portion.

Figure 10B:
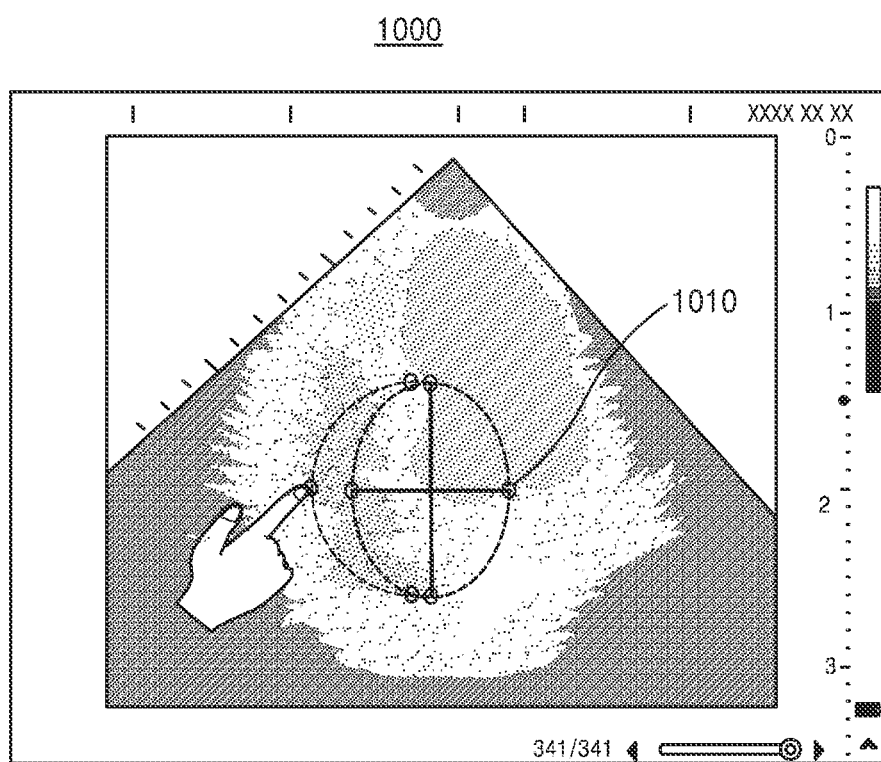
FIG. 10B is a view for describing a method of changing a configured measuring area in a direct change mode, via an ultrasound apparatus, according to an embodiment.

FIG. 10B is a view for describing a method of changing a configured measuring area, in a direct change mode, via the ultrasound apparatus 1000, according to an embodiment.

Referring to FIG. 10B, when the ultrasound apparatus 1000 receives a touch input with respect to the image 1010 indicating the measuring area, the ultrasound apparatus 1000 may change the configured measuring area. Also, the ultrasound apparatus 1000 may calculate a diameter, a circumferential length, and an area of a circle based on the changed measuring area.

Also, when the ultrasound apparatus 1000 receives a user input selecting a portion of the image 1010 indicating the measuring area and moving a position of the selected portion of the image 1010 in an ultrasound image, the ultrasound apparatus 1000 may change a position or a shape of the image 1010 indicating the measuring area, based on the position of the moved portion.

Also, the ultrasound apparatus 1000 may store the changed position of the measuring area and a measuring point.

Also, when receiving a user input selecting a scissors measuring device, the ultrasound apparatus 1000 may display a measuring device image, based on the stored position of the measuring point.

Figure 11A:
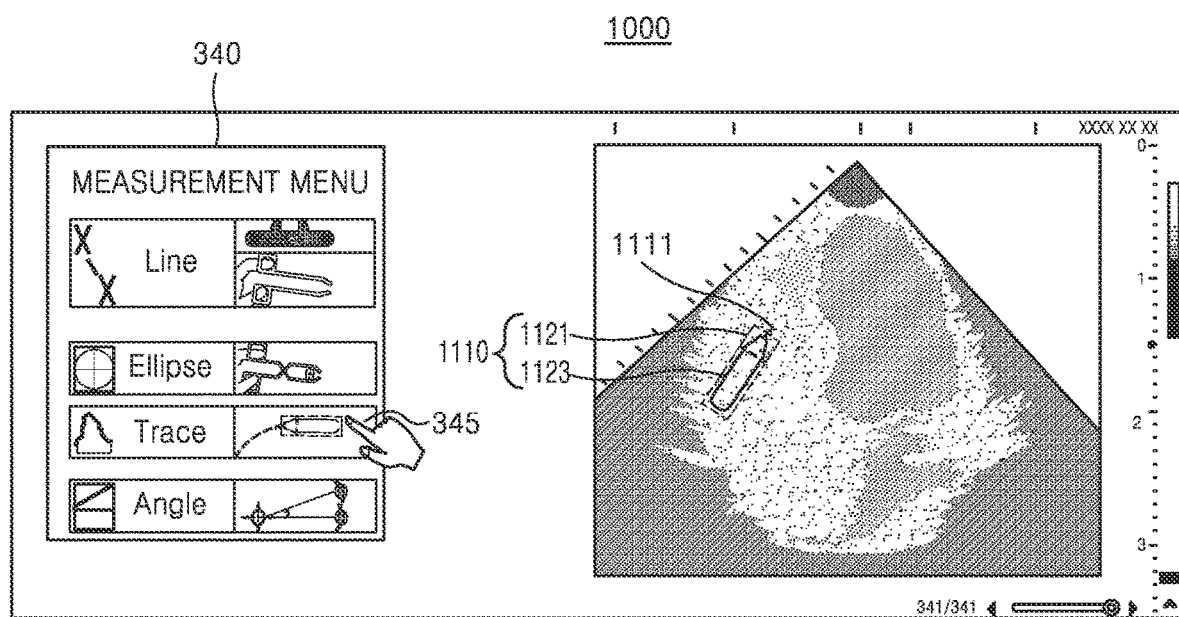
FIG. 11A is a view for describing a method of providing a measuring function via a pen measuring device, via an ultrasound apparatus, according to an embodiment.

FIG. 11A is a view for describing a method of providing a measuring function via a pen measuring device, via the ultrasound apparatus 1000, according to an embodiment.

Referring to FIG. 11A, when a pen measuring device icon 345 is selected, the ultrasound apparatus 1000 may display a pen measuring device image 1110 corresponding to the pen measuring device. The pen measuring device image 1110 may include a measuring point 1121 indicating a trace point 1111 in an ultrasound image and an adjusting portion 1123 receiving a user's touch input. The adjusting portion 1123 may be displayed in an adjusting area in the ultrasound image determining a position of the trance point 1111. Also, the ultrasound apparatus 1000 may determine a point that is apart from the adjusting area by a pre-determined distance as the trace point 1111.

The pen measuring device image 1110 corresponding to the pen measuring device may have a physical shape of a pen. Also, a position of the adjusting portion 1123 and the measuring point 1121 in the pen measuring device image 1110 may be pre-determined. For example, the adjusting portion 1123 may be a handle portion in the pen measuring device image 1110. Also, the measuring point 1121 may be a tip portion in the pen measuring device image 1110.

Figure 11B:
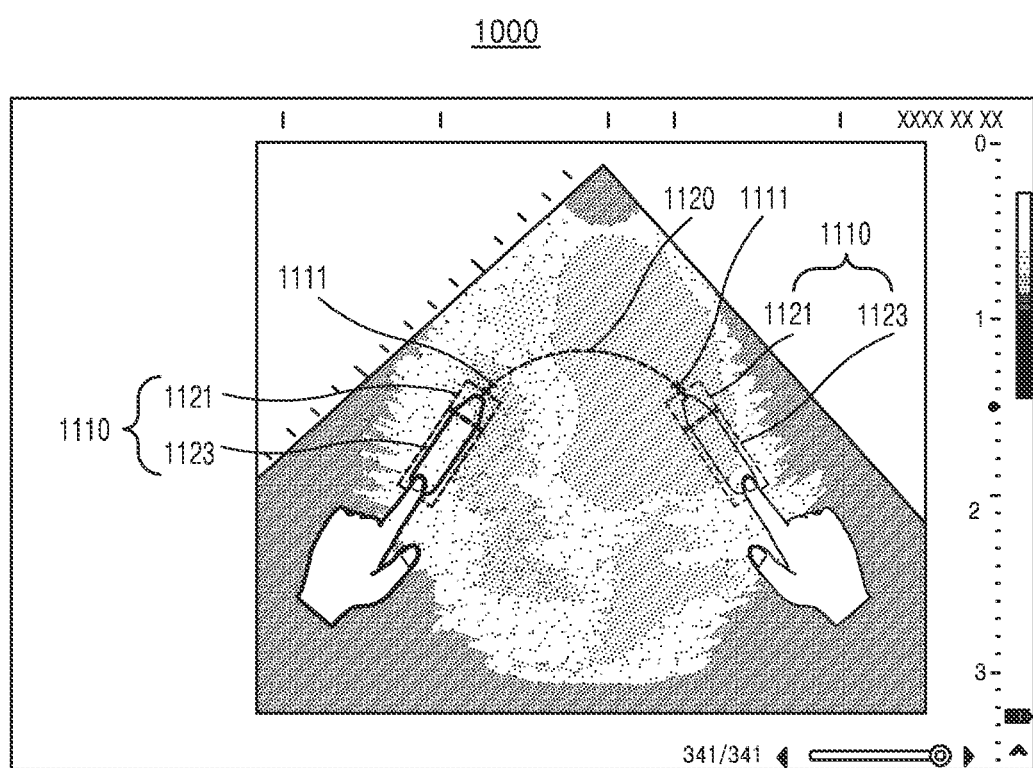
FIG. 11B is a view for describing a method of providing a trace function via a pen measuring device image, via an ultrasound apparatus, according to another embodiment.

FIG. 11B is a view for describing a method of providing a trace function via the pen measuring device image 1110, via the ultrasound apparatus 1000, according to another embodiment.

Referring to FIG. 11B, when receiving a touch input moving the pen measuring device image 1110, the ultrasound apparatus 1000 may determine a segment connecting the trace point 1111.

When receiving a touch input moving a position of the adjusting portion 1123 of the pen measuring device image 1110 in the ultrasound image, the ultrasound apparatus 1000 may move the pen measuring device image 1110 along the area touched by the user. Also, the ultrasound apparatus 1000 may determine a position of the trace point 1111, based on the position of the adjusting portion 1123.

Also, when receiving the touch input moving the position of the adjusting portion 1123 in the ultrasound image, the ultrasound apparatus 1000 may display a line image 1120 indicating the determined trace points 1111 on the ultrasound image.

Also, when receiving the touch input moving the position of the adjusting portion 1123 in the ultrasound image, the ultrasound apparatus 1000 may renew the line 1120 connecting the trace points 1111.

When the line 1120 connecting the trace points 1111 is renewed, the ultrasound apparatus 1000 may calculate a length of the renewed line 1120. Also, the ultrasound apparatus 1000 may calculate a displacement between a trace start point and a trace end point. Also, when the line 1120 connecting the trace points 1111 is a lopped curve, the ultrasound apparatus 1000 may calculate a minor axis, a major axis, a circumferential length, and an area of the looped curve.

Although it is not illustrated in FIG. 11B, the ultrasound apparatus 1000 may adjust a size of the pen measuring device image 1110. For example, when the ultrasound apparatus receives a long touch input with respect to the adjusting portion 1123 and a touch input dragging the adjusting portion 1123 in a lengthwise direction or the pen measuring device image 1110 or in the direction opposite thereto, the ultrasound apparatus 1000 may adjust the length of the pen measuring device image 1110. For example, when receiving the touch input extending the pen measuring device image 1110 in the lengthwise direction of the pen measuring device image 1110, the ultrasound apparatus 1000 may enlarge the size of the pen measuring device image 1110 by extending the pen measuring device image 1110 along the dragged area. Also, for example, when receiving the touch input decreasing the pen measuring device image 1110 in the direction opposite to the lengthwise direction of the pen measuring device image 1110, the ultrasound apparatus 1000 may decrease the pen measuring device image 1110 along the dragged area. For example, the ultrasound apparatus 1000 may change the pen measuring device image 1110 from 10 cm to 5 cm.

Figure 11C:
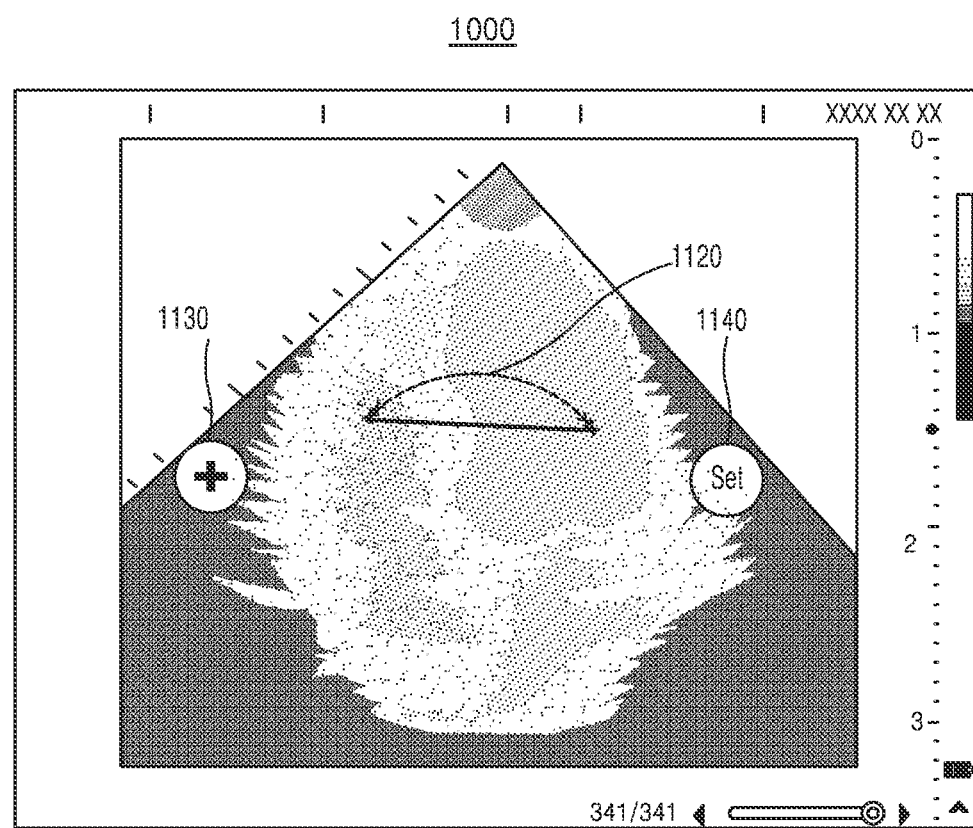
FIG. 11C is a view for describing a method of providing a trace function, via an ultrasound apparatus, according to another embodiment.

FIG. 11C is a view for describing a method of providing a trace function via the ultrasound apparatus 1000, according to another embodiment.

Referring to FIG. 11C, the ultrasound apparatus 1000 may display a button image 1130 for renewing the configured line 1120.

For example, when the touch input with respect to the pen measuring device image 1110 is ended, the ultrasound apparatus 1000 may delete the pen measuring device image 1110 and display the button image 1130 for renewing the configured line 1120. In this case, the ultrasound apparatus 1000 may not delete the image 1120 indicating the configured line 1120.

Also, when the touch input with respect to the pen measuring device image 1110 is ended, the ultrasound apparatus 1000 may display a button image 1140 for storing information with respect to the configured line 1120. The information with respect to the configured line 1120 may include the position of the trace points 1111 forming the configured line 1120 and a measurement value with respect to the line 1120.

When receiving the touch input selecting the button image 1130 for renewing the configured line 1120, the ultrasound apparatus 1000 may display the pen measuring device image 1110 on the ultrasound image such that the measuring point of the pen measuring device image 1110 indicates a start point or an end point of the configured line 1120. Also, when receiving the touch input moving the position of the adjusting portion in the ultrasound image, the ultrasound apparatus 1000 may renew the configured line 1120.

Figure 12A:
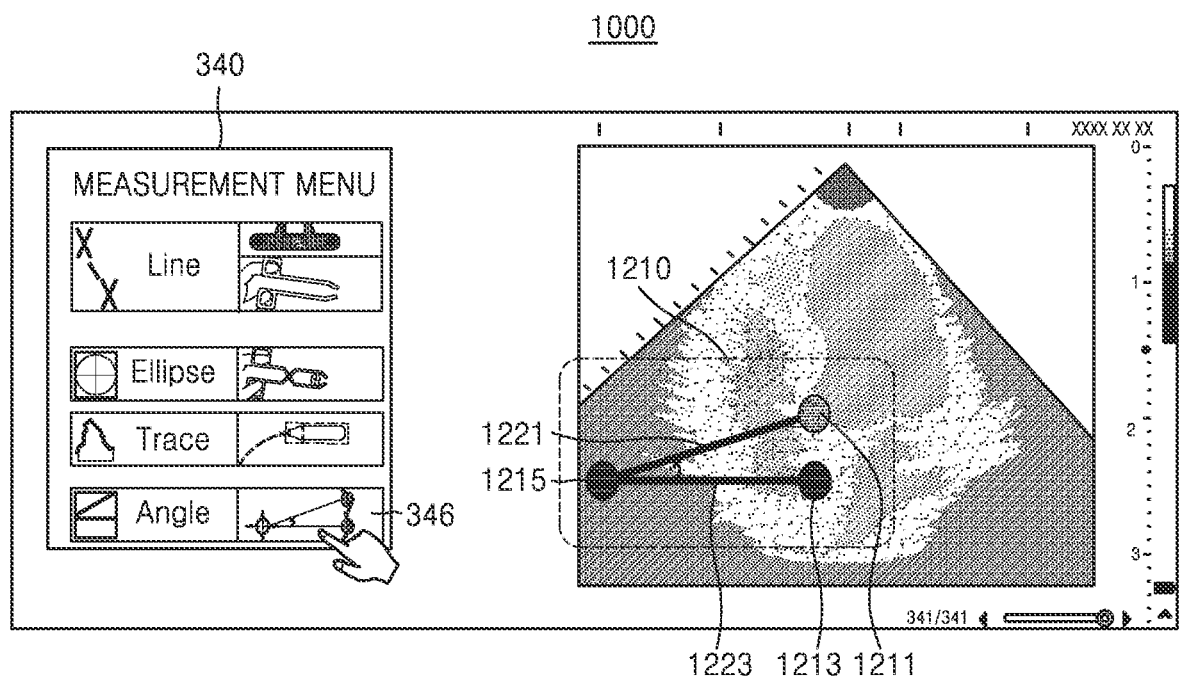
FIG. 12A is a view for describing a method of providing an angle measuring function, via an ultrasound apparatus, according to an embodiment.

FIG. 12A is a view for describing a method of providing an angle measuring function via the ultrasound apparatus 1000, according to an embodiment.

Referring to FIG. 12A, when an angle measuring device is selected, the ultrasound apparatus 1000 may display an angle measuring device image 1210 corresponding to the angle measuring device. The angle measuring device image 1210 may include two straight lines 1221 and 1223 generating an angle. Also, the angle measuring device image 1210 may include three adjusting portions 1211, 1213, and 1215. The three adjusting portions 1211, 1213, and 125 may be located at a vertex of a triangle formed by the two straight lines 1221 and 1223 and at end points of the two straight lines 1221 and 1223.

The ultrasound apparatus 1000 may measure the angle of the two straight lines 1221 and 1223. The ultrasound apparatus 1000 may measure the angle of the two straight lines 1221 and 1223 based on a position of the three adjusting portions 1211, 1213, and 125. For example, the ultrasound apparatus 1000 may measure the angle of the two straight lines 1221 and 1223 based on a position of the central point of the three adjusting portions 1211, 1213, and 1215.

Figure 12B:
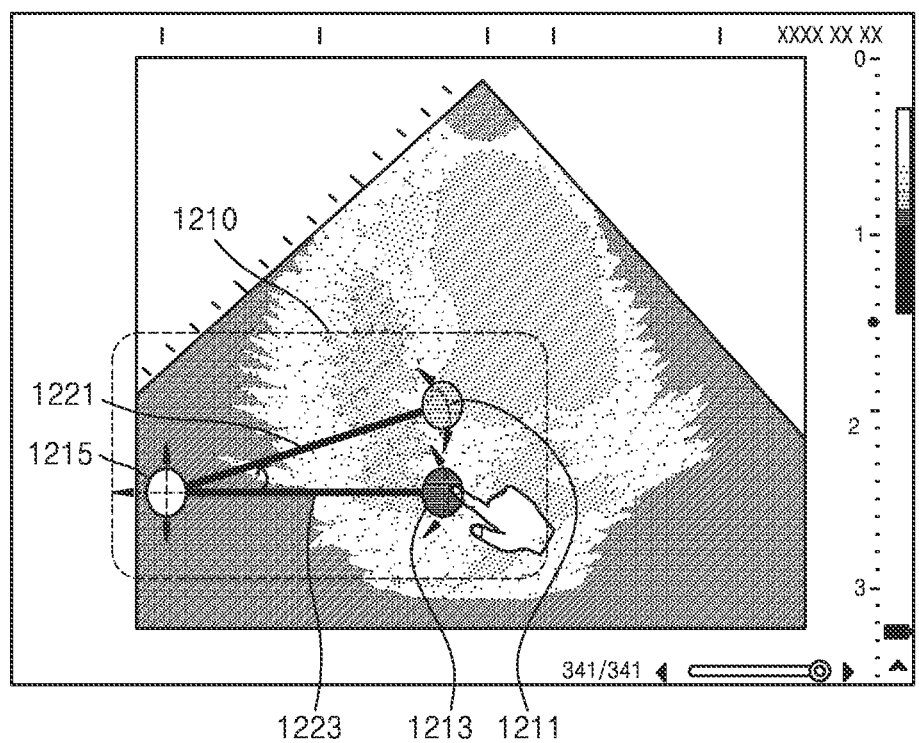
FIG. 12B is a view for describing a method of providing an angle measuring function, via an ultrasound apparatus, according to an embodiment.

FIG. 12B is a view for describing a method of providing an angle measuring function via the ultrasound apparatus 1000, according to an embodiment.

Referring to FIG. 12B, the ultrasound apparatus 1000 may change a position and a shape of the angle measuring device image 1210, when receiving a touch input moving the three adjusting portions 1211, 1213, and 1215, and may determine an angle of the two straight lines 1221 and 1223.

When receiving a touch input with respect to the adjusting portion 1215 located at the vertex formed by the two straight lines 1221 and 1223, the ultrasound apparatus 1000 may move the entire angle measuring device image 1210.

Also, when receiving a touch input with respect to the first adjusting portion 1211 on the first straight line 1221, the ultrasound apparatus 1000 may rotate the first straight line

1221 based on the vertex. Also, when receiving a touch input with respect to the second adjusting portion 1213 on the second straight line 1223, the ultrasound apparatus 1000 may rotate the second straight line 1223 based on the vertex.

When the position and the shape of the angle measuring device image 1210 are changed, the ultrasound apparatus 1000 may measure the angle formed by the two straight lines 1221 and 1223, based on the position of the three adjusting portions 1211, 1213, and 1215 in the angle measuring device image 1210.

Figure 13:
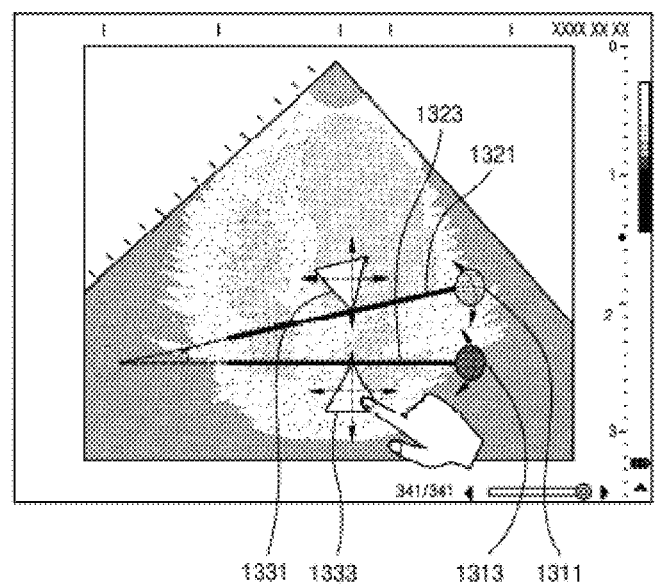
FIG. 13 is a view for describing a method of providing an angle measuring function, via an ultrasound apparatus, according to another embodiment.

FIG. 13 is a view for describing a method of providing an angle measuring function via the ultrasound apparatus 1000, according to another embodiment.

Referring to FIG. 13, when an angle measuring device is selected, the ultrasound apparatus 1000 may display an angle measuring device image 1310 corresponding to the angle measuring device.

The angle measuring device image 1310 may include two straight lines 1321 and 1323 generating an angle. Also, the angle measuring device image 1310 may include four adjusting portions 1311, 1313, 1331, and 1333. The four adjusting portions 1311, 1313, 1331, and 1333 may be located at end points of the two straight lines 1321 and 1323 and a middle point of the two straight lines 1221 and 1223.

The ultrasound apparatus 1000 may measure the angle formed by the two straight lines 1321 and 1323. For example, the ultrasound apparatus 1000 may determine a cross point at which the two straight lines 1321 and 1323 meet each other when the two straight lines 1321 and 1323 extend, based on a position of the end points of the two straight lines 1321 and 1323. When the cross point is determined, the ultrasound apparatus 1000 may calculate the angle formed by the two straight lines 1321 and 1323 at the cross point.

When the ultrasound apparatus 1000 receives a touch input with respect to the adjusting portion 1331 located in a middle point of the first straight line 1321, the ultrasound apparatus 1000 may move the entire first straight line 1321 in a parallel direction. Also, when the ultrasound apparatus 1000 receives a touch input with respect to the adjusting portion 1333 located in a middle point of the second straight line 1323, the ultrasound apparatus 1000 may move the entire second straight line 1323 in a parallel direction.

Also, when the ultrasound apparatus 1000 receives a touch input with respect to the adjusting portion 1311 located at an end point of the first straight line 1321, the ultrasound apparatus 1000 may rotate the first straight line 1321 based on the adjusting portion 1331 located in the middle point of the first straight line 1321. Also, when the ultrasound apparatus 1000 receives a touch input with respect to the adjusting portion 1313 located at an end point of the second straight line 1323, the ultrasound apparatus 1000 may rotate the second straight line 1323 based on the adjusting portion 1333 located in the middle position of the second straight line 1323.

When a position of the first straight line 1321 and the second straight line 1323 is changed, the ultrasound apparatus 1000 may determine a cross point of the first straight line 1321 and the second straight line 1323 or a cross point of extension lines of the first straight line 1321 and the second straight line 1323. Also, the ultrasound apparatus 1000 may calculate the angle formed by the first straight line 1321 and the second straight line 1323 based on the determined cross point.

Figure 14:
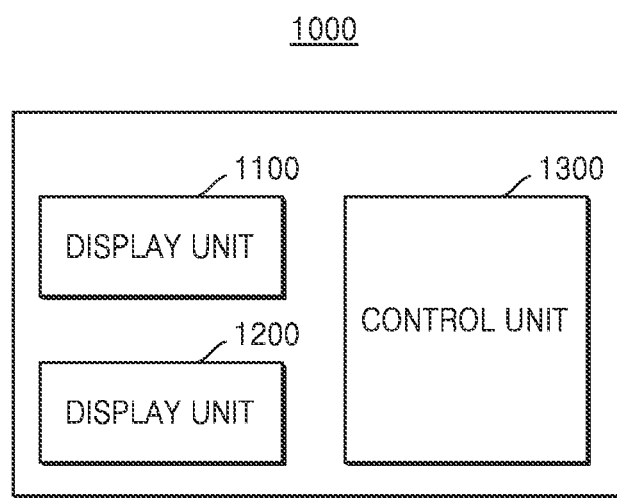
FIG. 14 is a block diagram of an ultrasound apparatus according to an embodiment.

FIG. 14 is a block diagram of the ultrasound apparatus 1000.

Referring to FIG. 14, the ultrasound apparatus 1000 may include a display unit 1100, a user input unit 1200, and a control unit 1300. However, not all of the illustrated components are essential. The ultrasound apparatus 1000 may be realized by more or less components that the illustrated components.

Hereinafter, the illustrated components will be described.

The display unit 1100 may display an ultrasound image and an image for a user interface.

The display unit 1100 may display on the ultrasound image a measuring device image including a plurality of measuring points indicating points in the ultrasound image that are to be measured, and adjusting portions for adjusting the plurality of measuring points. The measuring points may be disposed apart from the adjusting portions.

When a position of the adjusting portions and of the measuring point of the measuring device image is changed in the ultrasound image, the display unit 1100 may update the measuring device image, on a screen.

The user input unit 1200 may receive a touch input changing the position of the adjusting portion.

Also, the user input unit 1200 may receive a touch and drag input with respect to the adjusting portion.

The control unit 1300 may adjust a position of at least one of the plurality of measuring points based on the changed position of the adjusting portion and may obtain a measurement value based on a position of the plurality of measuring points including the at least one measuring point, the position of which is changed. Also, the control unit 1300 may adjust the position of the at least one of the plurality of measuring points by changing at least one of a position and a shape of the measuring device image.

For example, the control unit 1300 may adjust the position of the at least one of the plurality of measuring points by adjusting a length of the measuring device image, when the touch input changing the position of the adjusting portion is received.

For example, the control unit 1300 may adjust the position of the at least one of the plurality of measuring points by rotating the measuring device image, when the touch input changing the position of the adjusting portion is received.

For example, when the measuring device image includes two partial images crossing each other based on a reference point, the control unit 1300 may adjust the position of the at least one of the plurality of measuring points by rotating the two partial images based on the reference point.

Also, the control unit 1300 may generate a circle based on the position of the plurality of measuring points, and may calculate at least one of a diameter, a circumferential length, and an area of the generated circle.

Also, the display unit 1100 may display the obtained measurement value on the measuring device image.

Also, the display unit 1100 may display the measuring device image half-transparently so that an area of the ultrasound image, which overlaps the measuring device image, is not covered by the measuring device image. The display unit 1100 may display a button image for storing the measurement value, corresponding to the ultrasound image, on the ultrasound image.

Also, the display unit 1100 may delete the measuring device image and display a button image for re-adjusting the position of the plurality of measuring points, on the ultrasound image.

Figure 15:
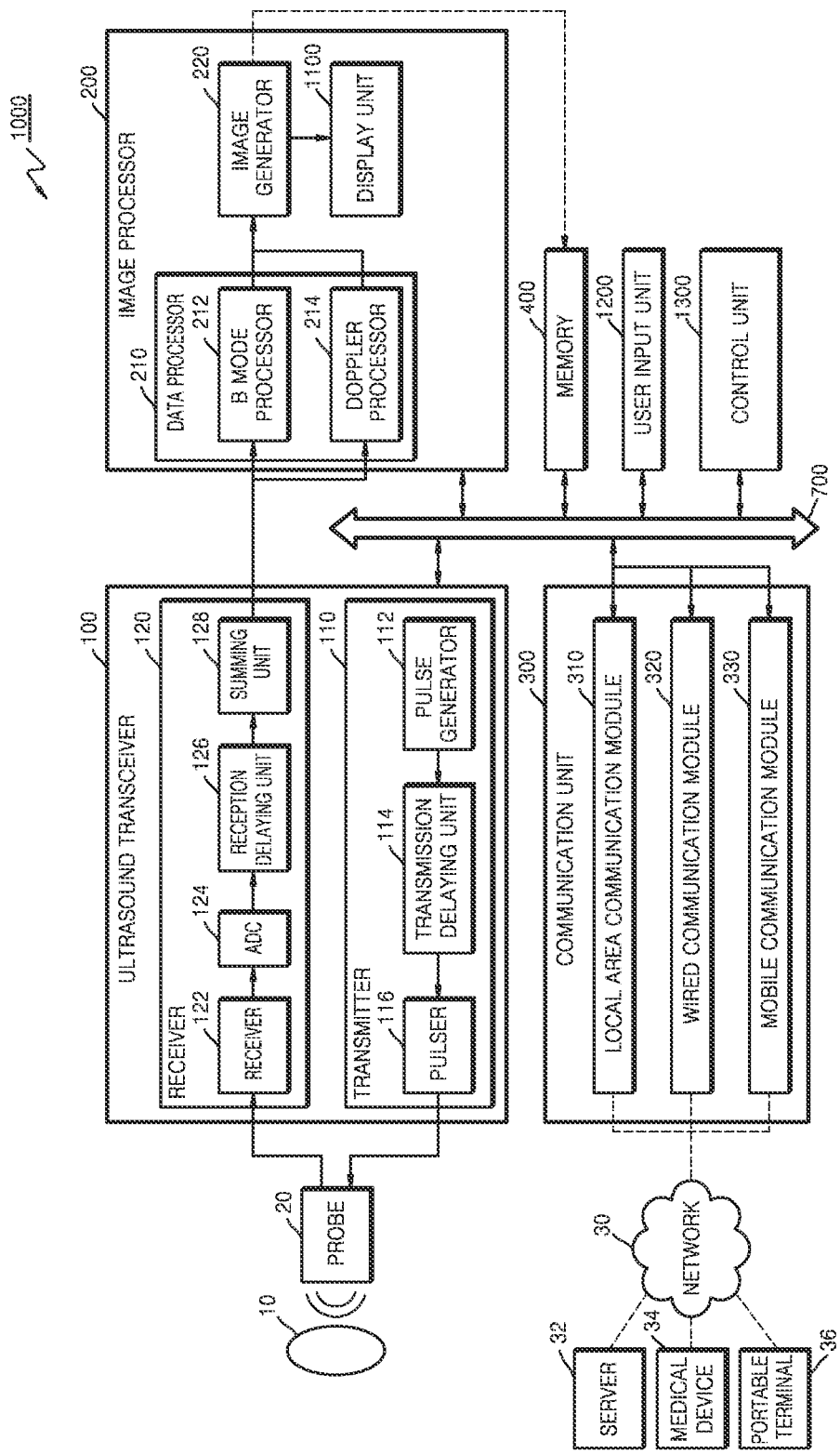
FIG. 15 is a block diagram of an ultrasound apparatus according to another embodiment.

FIG. 15 is a block diagram of the ultrasound apparatus 1000, according to another embodiment.

Referring to FIG. 15, the ultrasound apparatus 1000 may further include a probe 20, an ultrasound transceiver 100, an image processor 200, a communication unit 300, and a memory 400, in addition to the display unit 1100, the user input unit 1200, and the control unit 1300. The probe 20, the ultrasound transceiver 100, the image processor 200, the communication unit 300, the memory 400, the display unit 1100, the user input unit 1200, and the control unit 1300 may be connected with one another via a bus 700.

The ultrasound apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound apparatus 1000 by wire or wirelessly, and the ultrasound apparatus 1000 may include a plurality of probes 20 according to embodiments.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 166.

The image processor 200 generates an ultrasound image by scan-converting ultrasound data generated by the ultrasound transceiver 100 and displays the ultrasound image. The ultrasound image may be not only a grayscale ultrasound image obtained by scanning an object in an amplitude (A) mode, a brightness (B) mode, and a motion (M) mode, but also a Doppler image indicating a motion of the object. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 212 extracts B mode components from ultrasound data and processes the B mode components. An image generator 220 may generate an ultrasound image indicating signal intensities as brightness based on the extracted B mode components 212.

Similarly, a Doppler processor 214 may extract Doppler components from ultrasound data, and the image generator 220 may generate a Doppler image indicating a movement of an object as colors or waveforms based on the extracted Doppler components.

According to an embodiment, the image generator 220 may generate a three-dimensional (3D) ultrasound image via volume-rendering with respect to volume data and may also generate an elasticity image by imaging deformation of the object 10 due to pressure. Furthermore, the image generator 220 may display various pieces of additional information in an ultrasound image by using text and graphics. In addition, the generated ultrasound image may be stored in the memory 400.

In addition, the ultrasound apparatus 1000 may include two or more displays 1100 according to embodiments.

The communication module 300 is connected to a network 30 by wire or wirelessly to communicate with an external device or a server. The communication module 300 may exchange data with a hospital server or another medical apparatus in a hospital, which is connected thereto via a PACS. Furthermore, the communication module 300 may perform data communication according to the digital imaging and communications in medicine (DICOM) standard.

The communication module 300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 300 may receive information about a diagnosis history or medical treatment schedule of a patient from a server and utilizes the received information to diagnose the patient. Furthermore, the communication module 300 may perform data communication not only with a server or a medical apparatus in a hospital, but also with a portable terminal of a medical doctor or patient.

The communication module 300 is connected to the network 30 by wire or wirelessly to exchange data with a server 32, a medical apparatus 34, or a portable terminal 36. The communication module 300 may include one or more components for communication with external devices. For example, the communication module 1300 may include a local area communication module 310, a wired communication module 320, and a mobile communication module 330.

The local area communication module 310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 320 refers to a module for communication using electric signals or optical signals. Examples of wired communication techniques according to an embodiment may include communication via a twisted pair cable, a coaxial cable, an optical fiber cable, and an Ethernet cable.

The mobile communication module 330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 400 stores various data processed by the ultrasound apparatus 1000. For example, the memory 400 may store medical data related to diagnosis of an object, such as ultrasound data and an ultrasound image that are input or output, and may also store algorithms or programs which are to be executed in the ultrasound apparatus 1000.

The memory 400 may be any of various storage media, e.g., a flash memory, a hard disk drive, EEPROM, etc. Furthermore, the ultrasound apparatus 1000 may utilize web storage or a cloud server that performs the storage function of the memory 400 online.

The user input unit 1200 may further include various other input means including an electrocardiogram measuring module, a respiration measuring module, a voice recognition sensor, a gesture recognition sensor, a fingerprint recognition sensor, an iris recognition sensor, a depth sensor, a distance sensor, etc.

All or some of the probe 20, the ultrasound transceiver 100, the image processor 200, the communication module 300, the memory 400, the user input unit 1200, and the controller 1300 may be implemented as software modules. However, embodiments of the present invention are not limited thereto, and some of the components stated above may be implemented as hardware modules. Furthermore, at least one selected from the ultrasound transceiver 100, the image processor 200, and the communication module 300 may be included in the controller 1300. However, embodiments of the present invention are not limited thereto.

The method of the present invention may be implemented as computer instructions which may be executed by various computer means, and recorded on a computer-readable recording medium. The computer-readable recording medium may include program commands, data files, data structures, or a combination thereof. The program commands recorded on the computer-readable recording medium may be specially designed and constructed for the inventive concept or may be known to and usable by one of ordinary skill in a field of computer software. Examples of the computer-readable medium include storage media such as magnetic media (e.g., hard discs, floppy discs, or magnetic tapes), optical media (e.g., compact disc-read only memories (CD-ROMs), or digital versatile discs (DVDs)), magneto-optical media (e.g., floptical discs), and hardware devices that are specially configured to store and carry out program commands (e.g., ROMs, RAMs, or flash memories). Examples of the program commands include a high-level language code that may be executed by a computer using an interpreter as well as a machine language code made by a complier.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound apparatus comprising:
   a display configured to display, on an ultrasound image, a measuring device image, wherein the measuring device image comprises:
      a first adjusting portion and a second adjusting portion, on which a first touch input and a second touch input are received, respectively; and
      a first measuring point and a second measuring point which indicate points on the ultrasound image that are to be measured, the first measuring point being spaced apart from the first adjusting portion, the second measuring point being spaced apart from the second adjusting portion;
   a user input unit, comprising a touch panel, configured to receive the first touch input and the second touch input for changing positions of the first adjusting portion and the second adjusting portion, respectively;
   a controller, comprising an image processor, configured to:
      concurrently display the first measuring point and the second measuring point,
      adjust a position of the first measuring point upon receiving the first touch input for changing the position of the first adjusting portion,
      adjust a position of the second measuring point upon receiving the second touch input for changing the position of the second adjusting portion, and
      obtain a measurement value based on the adjusted positions of the first measuring point and the second measuring point,
   wherein, in an event where the first touch input for rotating the position of the first adjusting portion is received, the position of the second measuring point is fixed so that the position of the first measuring point rotates based on the second measuring point.

2. The ultrasound apparatus of claim 1, wherein a distance between the first measuring point and the first adjusting portion is maintained while the position of the first adjusting portion changes, and
   a distance between the second measuring point and the second adjusting portion is maintained while the position of the second adjusting portion changes.

3. The ultrasound apparatus of claim 1, wherein the first adjusting portion includes a first reference point, and the second adjusting portion includes a second reference point, and
   wherein the position of the first adjusting portion is configured to change with multiple degrees of freedom in relation to the first reference point, and the second adjusting portion is configured to change with multiple degrees of freedom in relation to the second reference point.

4. The ultrasound apparatus of claim 3,
   wherein, in an event where the second touch input for changing the position of the second adjusting portion received, the position of the first measuring point is fixed.

5. The ultrasound apparatus of claim 3, wherein the position of the first adjusting portion moves toward or away from the second reference point, and
   wherein the position of the second adjusting portion is configured to move toward or away from the first reference point.

6. The ultrasound apparatus of claim 1, wherein the controller is further configured to adjust the positions of the first measuring point and the second measuring point by adjusting a size of the measuring device image when the first touch input and the second touch input are received, respectively.

7. The ultrasound apparatus of claim 1, wherein the display is further configured to display the obtained measurement value on the measuring device image.

8. The ultrasound apparatus of claim 1, wherein the display is further configured to display the measuring device image in a partially-transparent way so that an area of the ultrasound image overlapping the measuring device image is not covered by the measuring device image.

9. The ultrasound apparatus of claim 1, wherein the first and second touch inputs for changing the positions of the first adjusting portion and the second adjusting portion comprise a user input of touching and dragging the first adjusting portion and the second adjusting portion.

10. The ultrasound apparatus of claim 9, wherein the user input unit is further configured to receive a touch input of ending the user input of touching and dragging the first adjusting portion and the second adjusting portion, and
the display is further configured to display on the ultrasound image a button image for storing the obtained measurement value in correspondence with the ultrasound image when the user input of touching and dragging the first adjusting portion and the second adjusting portion is ended.

11. The ultrasound apparatus of claim 9, wherein the user input unit is further configured to receive a touch input of ending the user input of touching and dragging the first adjusting portion and the second adjusting portion, and
the display is further configured to delete the measuring device image and display on the ultrasound image a button image for re-adjusting the positions of the first measuring point and the second measuring point when the user input of touching and dragging the first adjusting portion and the second adjusting portion is ended.

12. A method of processing an ultrasound image, the method comprising:
displaying, on an ultrasound image, a measuring device image, wherein the measuring device image comprises:
a first adjusting portion and a second adjusting portion, on which a first touch input and a second touch input are received, respectively; and
a first measuring point and a second measuring point which indicate points on the ultrasound image that are to be measured, the first measuring point being spaced apart from the first adjusting portion, the second measuring point being spaced apart from the second adjusting portion;
receiving the first touch input and the second touch input for changing positions of the first adjusting portion and the second adjusting portion, respectively;
concurrently display the first measuring point and the second measuring point;
adjusting a position of the first measuring point upon receiving the first touch input for changing the position of the first adjusting portion;
adjusting a position of the second measuring point upon receiving the second touch input for changing the position of the second adjusting portion; and
obtaining a measurement value based on the adjusted positions of the first measuring point and the second measuring point,
wherein, in an event where the first touch input for rotating the position of the first adjusting portion is received, the position of the second measuring point is fixed so that the position of the first measuring point rotates based on the second measuring point.

13. The ultrasound apparatus of claim 12, wherein a distance between the first measuring point and the first adjusting portion is maintained while the position of the first adjusting portion changes, and
a distance between the second measuring point and the second adjusting portion is maintained while the position of the second adjusting portion changes.

14. The method of claim 12, wherein the first adjusting portion includes a first reference point, and the second adjusting portion includes a second reference point, and
wherein the position of the first adjusting portion is configured to change with multiple degrees of freedom in relation to the first reference point, and the second adjusting portion is configured to change with multiple degrees of freedom in relation to the second reference point.

15. The method of claim 14,
wherein, in an event where the second touch input for changing the position of the second adjusting portion received, the position of the first measuring point is fixed.

16. The method of claim 14, wherein the position of the first adjusting portion moves toward or away from the second reference point, and
wherein the position of the second adjusting portion is configured to move toward or away from the first reference point.

17. The method of claim 12, further comprising adjusting the positions of the first measuring point and the second measuring point by adjusting a size of the measuring device image when the first touch input and the second touch input are received, respectively.

18. The method of claim 12, further comprising displaying the obtained measurement value on the measuring device image.

19. The method of claim 12, wherein the displaying comprises displaying the measuring device image in a partially-transparent way so that an area of the ultrasound image overlapping the measuring device image is not covered by the measuring device image.

20. The method of claim 12, wherein the first and second touch inputs for changing the positions of the first adjusting portion and the second adjusting portion comprise a user input of touching and dragging the first adjusting portion and the second adjusting portion.

21. The method of claim 20, further comprising:
receiving a touch input of ending the user input of touching and dragging the first adjusting portion and the second adjusting portion; and
displaying on the ultrasound image a button image for storing the obtained measurement value in correspondence with the ultrasound image when the user input of touching and dragging the first adjusting portion and the second adjusting portion is ended.

22. The method of claim 20, further comprising:
receiving a touch input of ending the user input of touching and dragging the first adjusting portion and the second adjusting portion; and
deleting the measuring device image and displaying on the ultrasound image a button image for re-adjusting the positions of the first measuring point and the second measuring point when the user input of touching and dragging the first adjusting portion and the second adjusting portion is ended.

* * * * *